US011275089B2

(12) United States Patent
Jain et al.

(10) Patent No.: US 11,275,089 B2
(45) Date of Patent: Mar. 15, 2022

(54) PLASMONIC NANOPARTICLES, METHODS OF MAKING PLASMONIC NANOPARTICLES AND SENSORS MADE THEREFROM

(71) Applicant: UNM RAINFOREST INNOVATIONS, Albuquerque, NM (US)

(72) Inventors: Ravinder Jain, Albuquerque, NM (US); Abhaya K. Datye, Albuquerque, NM (US); Ying-Bing Jiang, Albuquerque, NM (US)

(*) Notice: Subject to any disclaimer, the term of this patent is extended or adjusted under 35 U.S.C. 154(b) by 433 days.

(21) Appl. No.: 15/801,070

(22) Filed: Nov. 1, 2017

(65) Prior Publication Data
US 2019/0128894 A1 May 2, 2019

Related U.S. Application Data

(60) Provisional application No. 62/415,953, filed on Nov. 1, 2016.

(51) Int. Cl.
| | |
|---|---|
| *G01N 33/58* | (2006.01) |
| *A61K 41/00* | (2020.01) |
| *A61K 9/51* | (2006.01) |
| *A61P 35/00* | (2006.01) |
| *G01N 33/84* | (2006.01) |
| *G01N 21/65* | (2006.01) |
| *G01N 21/64* | (2006.01) |
| *C23C 16/455* | (2006.01) |
| *B82Y 5/00* | (2011.01) |
| *B82Y 20/00* | (2011.01) |
| *B82Y 40/00* | (2011.01) |

(52) U.S. Cl.
CPC .......... *G01N 33/588* (2013.01); *A61K 9/5115* (2013.01); *A61K 41/008* (2013.01); *A61P 35/00* (2018.01); *C23C 16/45525* (2013.01); *G01N 21/6489* (2013.01); *G01N 21/658* (2013.01); *G01N 33/84* (2013.01); *B82Y 5/00* (2013.01); *B82Y 20/00* (2013.01); *B82Y 40/00* (2013.01); *Y10S 977/774* (2013.01); *Y10S 977/81* (2013.01); *Y10S 977/824* (2013.01); *Y10S 977/891* (2013.01)

(58) Field of Classification Search
CPC .... A61K 9/143; A61K 9/1611; A61K 9/1682; G01N 33/588
See application file for complete search history.

(56) References Cited

U.S. PATENT DOCUMENTS

| | | | | |
|---|---|---|---|---|
| 8,012,860 B2 * | 9/2011 | Elam | ................... | H01L 21/0262 438/481 |
| 9,267,889 B1 | 2/2016 | Klopfer et al. | | |
| 2012/0273662 A1 * | 11/2012 | Caldwell | .............. | G01N 21/658 250/214.1 |
| 2013/0003058 A1 * | 1/2013 | Van Dorpe | ............ | B82Y 15/00 356/301 |
| 2015/0072085 A1 * | 3/2015 | Lansalot-Matras | ........................ | C23C 16/45553 427/576 |
| 2015/0108245 A1 * | 4/2015 | Martinez | ............... | E03C 1/0408 239/75 |
| 2015/0108425 A1 * | 4/2015 | Rosenman | ............ | H01L 27/307 257/13 |
| 2016/0050750 A1 * | 2/2016 | Rogers | ................. | H05K 1/0286 361/767 |
| 2018/0122648 A1 * | 5/2018 | Kim | .................... | H01L 21/3086 |

OTHER PUBLICATIONS

Aaltonen et al., "Atomic Layer Deposition of Noble Metal Thin Films," Ph.D. Dissertation, University of Helsinki, Finland. 2005.
Alabi et al., "Perspectives on Kiss-and-Run: Role in Exocytosis, Endocytosis, and Neurotransmission," Annual Review of Physiology 75, 393-422 (2013).
Averitt et al., "Plasmon Resonance Shifts of Au-Coated $Au_2S$ Nanoshells: Insight into Multicomponent Nanoparticle Growth," Phys. Rev. Lett. 78, 4217-4220 (1997).
Baker et al., "Growth of Continuous and Ultrathin Platinum Films on Tungsten Adhesion Layers using Atomic Layer Deposition Techniques," Appl. Phys. Letts, 101(11) (2012).
Baker et al., "Protein and acidosis alter calcium-binding and fluorescence spectra of the calcium indicator indo-1," Biophysical Journal 67, 1646-1654 (1994).
Bamwenda et al., "The influence of the preparation methods on the catalytic activity of platinum and gold supported on $TiO_2$; for CO oxidation," Catalysis Letters 44, 83-87 (1997).
Berridge et al., "Calcium Signalling Dynamics, Homeostatis and Remodelling," Nature Reviews, Molecular Cell Biology 4, 517-529 (Jul. 2003).
Bishnoi et al., "All-Optical Nanoscale pH Meter," Nano Letters, 6(8), 1687-1692, doi:doi:10.1021/nl060865w, 2006.
Bore et al., "The Role of Pore Size and Structure on the Thermal Stability of Gold Nanoparticles within Mesoporous Silica," J. Phys. Chem. B 109, 2873-2880 (2005).
Boulanger et al., "Focus Issue Introduction: Nonlinear Optics," Optics Express 19 (23): 23561-23566 (2011).
Brinson et al., "Nanoshells Made Easy: Improving Au Layer Growth on Nanoparticle Surfaces," Langmuir 24 (24) (Dec. 16, 2008): 14166-14171. doi:10.1021/la802049p.

(Continued)

Primary Examiner — Micah Paul Young
(74) Attorney, Agent, or Firm — MH2 Technology Law Group LLP

(57) ABSTRACT

A method of making free-standing ALD-coated plasmonic nanoparticles. The method comprises providing a plurality of semiconductor quantum dots. One or more conformal layers of dielectric material are deposited over the quantum dots to form dielectric-coated quantum dots. A conformal metallic nanoshell is deposited over the dielectric-coated quantum dots to form plasmonic nanoparticles. At least one layer chosen from i) the conformal layers of dielectric material and ii) the conformal metallic nanoshell is deposited using a vapor phase atomic layer deposition (ALD) process. Plasmonic nanoparticles and systems employing the nanoparticles are also disclosed.

25 Claims, 8 Drawing Sheets

(56) References Cited

OTHER PUBLICATIONS

Brito-Silva et al., "Improved Synthesis of Gold and Silver Nanoshells." Langmuir 29 (13) (Apr. 2, 2013): 4366-4372. doi:10.1021/la3050626.
Bronk et al., "Differential effects of SNAP-25 deletion on Ca2+-dependent and Ca2+-independent neurotransmission," Journal of Neurophysiology, 98(2), 794-806 (2007).
Brown et al., "In Vivo Measurement of Gene Expression, Angiogenesis and Physiological Function in Tumors Using Multiphoton Laser Scanning Microscopy," Nature Medicine 7 (7) (Jul. 1): 864-868. doi:10.1038/89997.BRUCHEZ, Bruchez, M., Moronne, M., Gin, P., Weiss, S. & Alivisatos, A. P. Semiconductor Nanocrystals as Fluorescent Biological Labels. Science 281, 2013-2016 (1998).
Bunge et al., "Growth and Morphology of Cadmium Chalcogenides: The Synthesis of Nanorods, Tetrapods, and Spheres from CdO and Cd (O2CCH3) 2," J. Mater. Chem. 13 (7): 1705-1709 (2003).
Burton et al., "Surfactant-free synthesis of Pd nanoparticles for heterogeneous catalysts," Journal of Catalysis 280, 145-149 (2011).
Calaet al., "Cell volume and pH regulation by the Amphiuma red blood cell: A model for hypoxia-induced cell injury," Comparative Biochemistry and Physiology Part A: Physiology, 102(4), 603-608, doi:doi: DOI: 10.1016/0300-9629(92)90711-X, 1992.
Canneson et al., "Enhancing the Fluorescence of Individual Thick Shell CdSe/CdS Nanocrystals by Coupling to Gold Structures," *New Journal of Physics* 14 (6) (Jun. 1, 2012): 063035. doi:10.1088/1367-2630/14/6/063035.
Casey et al., "Sensors and regulators of intracellular pH," Nat Rev Mol Cell Biol, 11(1), 50-61, doi:10.1038/nrm2820, 2010.
Casson et al., "Electro-optic Coefficients of Lithium Tantalate at Near-infrared Wavelengths," Journal of the Optical Society of America B 21 (11) (Nov. 1, 2004): 1948-1952. doi:10.1364/JOSAB.21.001948.
Centonze et al., "Multiphoton Excitation Provides Optical Sections from Deeper within Scattering Specimens than Confocal Imaging," Biophysical Journal 75, 2015-2024 (1998).
Chan et al., "Quantum Dot Bioconjugates for Ultrasensitive Nonisotopic Detection," Science 281, 2016-2018 (1998).
Chen et al., "Imaging High-Resolution Structure of GFP-Expressing Neurons in Neocortex In Vivo," Learning & Memory 7 (6) (Nov. 1, 2000): 433-441. doi:10.1101/lm.32700.
Chen et al., "Fluorescent CdSe/ZnS Nanocrystal-Peptide Conjugates for Long-term, Nontoxic Imaging and Nuclear Targeting in Living Cells," Nano Lett. 4, 1827-1832 (2004).
Chen et al., "Giant" multishell CdSe nanocrystal quantum dots with suppressed blinking, Journal of the American Chemical Society, 130(15), 5026-5027, 2008.
Chen et al., "Near-IR emission from metal-insulator-metal tunnel junctions based on surface plasmon interactions," Conference on Lasers and Electro-Optics, 2009 and 2009 Conference on Quantum electronics and Laser Science Conference. CLEO/QELS 2009 1-2 (2009).
Clark et al., "Optical Nanosensors for Chemical Analysis inside Single Living Cells. 1. Fabrication, Characterization, and Methods for Intracellular Delivery of PEBBLE Sensors," Analytical Chemistry, 71(21), 4831-4836, doi:doi:10.1021/ac990629o, 1999.
Coyle et al., "Thermally Robust Gold and Silver Iminopyrrolidinates for Chemical Vapor Deposition of Metal Films," Chem. of Materials, 25, 4566-4573, (2013).
Danek et al., "Synthesis of Luminescent Thin-Film CdSe/ZnSe Quantum Dot Composites Using CdSe Quantum Dots Passivated with an Overlayer of ZnSe," Chem. Mater. 8, 173-180 (1996).
De Grauw et al., "Line-scan Raman microspectrometry for biological applications," Applied Spectroscopy, 51(11), 1607-1612, 1997.
Delehanty et al, "Delivering quantum dot-peptide bioconjugates to the cellular cytosol: escaping from the endolysosomal system," Integr. Biol., 2(5-6), 265-277, 2010.
Dement'eva et al., "Colloidal synthesis of new silver-based nanostructures with tailored localized surface plasmon resonance," Colloid Journal 73, 724-742 (2011).
Deng et al., "Penetration Depth of Single-, Two-, and Three-Photon Fluorescence Microscopic Imaging through Human Cortex Structures: Monte Carlo Simulation," Appl. Opt. 42, 3321-3329 (2003).
Denk et al., "Two-photon laser scanning fluorescence microscopy," Science 248, 73-76 (1990).
Diaspro et al., "Multi-photon Excitation Microscopy." BioMedical Engineering, OnLine 5 (1): 1-14. doi:10.1186/1475-925X-5-36 (2006).
Dunn et al., "Functional Studies of the Kidney of Living Animals Using Multicolor Two-photon Microscopy," American Journal of Physiology—Cell Physiology 283 (3) (Sep. 1): C905-C916. doi:10.1152/ajpcell.00159 (2002).
Durr et al., "Two-Photon Luminescence Imaging of Cancer Cells Using Molecularly Targeted Gold Nanorods," Nano Letters 7 (4) (Apr. 1, 2007): 941-945. doi:10.1021/nl062962v.
Efros et al., "The Electronic Structure of Semiconductor Nanocrystals1," Annual Review of Materials Science 30, 475-521 (2000).
Elam et al., "Conformal Coating on Ultrahigh-aspect-ratio Nanopores of Anodic Alumina by Atomic Layer Deposition," *Chemistry of Materials*, 15 (18), 3507-3517 (2003).
Elsheikha et al., "Assessment of Sarcocystis neurona Sporocyst Viability and Differentiation Between Viable and Nonviable Sporocysts Using Propidium Iodide Stain," Journal of Parasitology 90, 872-875 (2004).
Enderlein, "J. Spectral properties of a fluorescing molecule within a spherical metallic nanocavity," Phys. Chem. Chem. Phys. 4, 2780-2786 (2002).
English et al., "A novel method for the synthesis of monodisperse gold-coated silica nanoparticles," J Nanopart Res 14, 1-10 (2012).
Foley et al., "Apoptosis in the cortex of the developing mouse kidney," Journal of Anatomy 201, 477-484 (2002).
Gatenby et al., A microevolutionary model of carcinogenesis, Nat Rev Cancer, 8(1), 56-61, doi:10.1038/nrc2255, 2008.
George, Atomic Layer Deposition: An Overview, Chem. Rev. (110), 111-131, (2010).
Gerion et al., "Synthesis and Properties of Biocompatible Water-Soluble Silica-Coated CdSe/ZnS Semiconductor Quantum Dots," The Journal of Physical Chemistry B 105 (37) (Sep. 1, 2001): 8861-8871. doi:10.1021/jp0105488.
Geisow et al., Fluorescein conjugates as indicators of subcellular pH : A critical evaluation, Experimental Cell Research, 150(1), 29-35, doi:doi: DOI: 10.1016/0014-4827(84)90698-0, 1984.
Gallud, "Functionalized Nanoparticles for Drug Delivery, One- and Two-photon Photodynamic Therapy as a Promising Treatment of Retinoblastoma," *Journal of Clinical & Experimental Ophthalmology* 04, (2013).
Gao et al., Nanoparticles for Two-Photon Photodynamic Therapy in Living Cells. *Nano Lett.* 6, 2383-2386 (2006).
Gerung et al., "Two-photon absorption of matrix-free Ge nanocrystals," Applied Physics Letters 89, 111107-111107-3 (2006).
Gerweck et al., "Cellular pH Gradient in Tumor versus Normal Tissue: Potential Exploitation for the Treatment of Cancer," Cancer Research, 56(6), 1194-1198, 1996.
Graham et al., "Molecular Analysis of SNAP-25 Function in Exocytosis," Annals of the New York Academy of Sciences, 971(1), 210-221 (2002).
Grainger et al., "Intracellular pH controls protein synthesis rate in the sea urchin egg and early embryo," Developmental Biology, 68(2),396-406, doi:doi: DOI: 10.1016/0012-1606(79)90213-6, 1979.
Gueroui et al., "Single-molecule measurements of gold-quenched quantum dots," Phys. Rev. Lett., 93(16), 166108-1-4, doi:10.1103/PhysRevLett.93.166108, 2004.
Guerrero-Martínez et al., "Recent Progress on Silica Coating of Nanoparticles and Related Nanomaterials," Advanced Materials 22, 1182-1195 (2010).
Guo et al., "Conjugation Chemistry and Bioapplications of Semiconductor Box Nanocrystals Prepared via Dendrimer Bridging," Chem. Mater. 15, 3125-3133 (2003).
Hakim et al., Nanocoating Individual Silica Nanoparticles by Atomic Layer Deposition in a Fluidized Bed Reactor, Chem. Vap. Dep. 11, 420-425, 2005.
Halas et al., "A Plethora of Plasmonics from the Laboratory for Nanophotonics at Rice University." Advanced Materials 24 (36): 4842-4877. doi:10.1002/adma.201202331 (2012).

(56) References Cited

OTHER PUBLICATIONS

Hamalainen et al., Atomic Layer Deposition of Noble Metals and Their Oxides, Chem. of Materials 26, 786-801, (2014).
Haugland, Handbook of Fluorescent Probes and Research Chemicals, 5th ed., Molecular Probes, 1992.
Herman, "Fluorescence microscopy," 2nd ed., Garland Science., 1997.
Hove-Madsen et al., Indo-1 binding to protein in permeabilized ventricular myocytes alters its spectral and Ca binding properties. Biophysical Journal, 63(1), 89-97 (Jul. 1992).
Hövel et al., Dielectric properties of ultrathin metal films around the percolation threshold. Phys. Rev. B 81, 035402 (2010).
Hu et al., Surface-enhanced Raman spectroscopy study on the structure changes of 4-mercaptopyridine adsorbed on silver substrates and silver colloids, Spectrochimica Acta Part A: Molecular and Biomolecular Spectroscopy, 58, 2827-2834, doi:10.1016/S1386-1425(02)00074-4, 2002.
Huang et al., Transdermal immunization with low-pressure-gene-gun mediated chitosan-based DNA vaccines against Japanese encephalitis virus, Biomaterials, 30(30), 6017-6025, doi:10.1016/j.biomaterials. 2009.07.029, 2009.
Huber et al., Proton dynamics in cancer, Journal of Translational Medicine, 8(1), 57, 2010.
Jackson, et al., Controlling the surface enhanced Raman effect via the nanoshell geometry. Applied Physics Letters 82, 257-259 (2003).
Jackson, et al., Quantum dots are phagocytized by macrophages and colocalize with experimental gliomas, Neurosurgery, 60(3), 524-529;discussion 529-530, doi:10.1227/01.NEU.0000255334.95532. DD, 2007.
Jankiewicz, et al., Silica-metal core-shell nanostructures. Advances in Colloid and Interface Science 170, 28-47 (2012).
Ji, et al., Synthesis and application of submicrometer fluorescence sensing particles for lysosomal pH measurements in murine macrophages, Analytical Chemistry, 72(15), 3497-3503, 2000.
Jiang, et al., Optimizing the Synthesis of Red- to Near-IR-Emitting CdS-Capped $CdTe_xSe_{1-x}$ Alloyed Quantum Dots for Biomedical Imaging. Chem. Mater. 18, 4845-4854 (2006).
Jin, et al., Plasmonic fluorescent quantum dots. Nature Nanotechnology 4, 571-576 (2009).
Johnson, et al., A brief review of atomic layer deposition: from fundamentals to applications, Materials Today 17 (5), 236-246, (2014).
K'owino, et al., Metal-enhanced biosensor for genetic mismatch detection, Analytical Biochemistry, 369(1), 8-17, doi:doi: DOI: 10.1016/j.ab.2007.06.046, 2007.
Kah, et al., "Synthesis of Gold Nanoshells Based on the Depositionprecipitation Process." Gold Bulletin 41 (1): 23-36. doi:10.1007/BF03215620 (2008).
Kang, et al., "Confinement-induced Valence-band Mixing in CdS Quantum Dots Observed by Two-photon Spectroscopy." Physical Review B 45 (7) (Feb. 1992): 3465-3468. doi:10.1103/PhysRevB. 45.3465.
Kerker, et al., Elastic scattering, absorption, and surface-enhanced Raman scattering by concentric spheres comprised of a metallic and a dielectric region. Phys. Rev. B 26, 4052-4063 (1982).
Kim, et al., Preparation, Characterization, and Optical Properties of Gold, Silver, and Gold-Silver Alloy Nanoshells Having Silica Cores. Langmuir 24, 11147-11152 (2008).
Klopfer, et al., Plasmonic Quantum Dots for Nonlinear Optical Applications. Nonlinear Optics: Materials, Fundamentals and Applications NThB3 (2011).
Klopfer, et al., Plasmonic quantum dots for nonlinear optical applications [Invited]. Opt. Mater. Express 1, 1353-1366 (2011).
Kneipp, et al., SERS—a single-molecule and nanoscale tool for bioanalytics. *Chem. Soc. Rev.* 37, 1052-1060 (2008).
Kodali, et al., Optimally designed nanolayered metal-dielectric particles as probes for massively multiplexed and ultrasensitive molecular assays. PNAS 107, 13620-13625 (2010).

Koole, et al., "On the Incorporation Mechanism of Hydrophobic Quantum Dots in Silica Spheres by a Reverse Microemulsion Method." Chemistry of Materials 20 (7) (Apr. 1, 2008): 2503-2512. doi:10.1021/cm703348y.
Kraus, et al., Plasmon resonance broadening in small metal particles. The Journal of Chemical Physics 79, 6130-6139 (1983).
Kumari, et al., New Nano Architecture for SERS Applications. J. Phys. Chem. Lett. 3, 1130-1135 (2012).
Larson, et al., "Water-Soluble Quantum Dots for Multiphoton Fluorescence Imaging in Vivo," Science 300 (5624) (May 30, 2003): 1434-1436. doi:10.1126/science.1083780.
Lee, et al., "Nanoparticle PEBBLE Sensors in Live Cells and In Vivo," Annual Review of Analytical Chemistry,2(1),57-76, doi:doi: 10.1146/annurev.anchem.1.031207.112823, 2009.
Leroueil, et al., Nanoparticle Interaction with Biological Membranes: Does Nanotechnology Present a Janus Face?, Accounts of Chemical Research, 40(5), 335-342, doi:doi: 10.1021/ar600012y, 2007.
Levene, et al., Vivo Multiphoton Microscopy of Deep Brain Tissue. J Neurophysiol 91, 1908-1912 (2004).
Li, et al., "Development of Methodology Based on the Formation Process of Gold Nanoshells for Detecting Hydrogen Peroxide Scavenging Activity," Anal. Chem. 81, 8916-8922 (2009).
Li, et al., "pHTomato, a red, genetically encoded indicator that enables multiplex interrogation of synaptic activity." Nature Neuroscience,15(7), 1047-1053 (2012).
Liaw, et al., "Plasmonic effect of nanoshelled nanocavity on encapsulated emitter's spontaneous emission," Journal of Quantitative Spectroscopy and Radiative Transfer 112, 2480-2485 (2011).
Liaw, et al., "Bi-dipole emission via plasmon modes of Au/Ag nanoshell," *Journal of Quantitative Spectroscopy and Radiative Transfer* (2012).
Lin, et al., Fluorescence lifetime-resolved pH imaging of living cells. *Cytometry Part A* 52A, 77-89 (2003).
Liu, et al., pH-sensing nanostar probe using surface-enhanced Raman scattering (SERS): theoretical and experimental studies. *Journal of Raman Spectroscopy* 44, 980-986 (2013).
Martínez-Zaguilán, et al, "Acidic pH enhances the invasive behavior of human melanoma cells," Clinical and Experimental Metastasis, 14(2), 176-186, 1996.
Masters, et al., "Optical Biopsy of In Vivo Human Skin: Multiphoton Excitation Microscopy," Lasers in Medical Science 13, 196-203 (1998).
McCombs, et al., "Measuring calcium dynamics in living cells with genetically encodable calcium indicators," Methods,46(3), 152-159.
Miao, et al., Nanocomposite plasmonic fluorescence emitters with core/shell configurations. J. Opt. Soc. Am. B 27, 1561-1570 (2010).
Miyawaki, et al., "Fluorescent indicators for Ca2+based on green fluorescent proteins and calmodulin," Nature, 388(6645), 882-887, (1997).
Moroz, "A. Electron Mean Free Path in a Spherical Shell Geometry," J. Phys. Chem. C 112, 10641-10652 (2008).
Mukherjee, et al., "Endocytosis," American Physiological Reviews, 77 (3), 759-804 (1997).
Murray, et al., "Synthesis and characterization of nearly monodisperse CdE (E=sulfur, selenium, tellurium) semiconductor nanocrystallites," J. Am. Chem. Soc. 115, 8706-8715 (1993).
Mwilu, et al., "Identification and quantitation of Bacillus globigii using metal enhanced electrochemical detection and capillary biosensor," Analytical Chemistry, 81(18), 7561-7570, 2009.
Nabiev, et al., "Nonfunctionalized Nanocrystals Can Exploit a Cell's Active Transport Machinery Delivering Them to Specific Nuclear and Cytoplasmic Compartments." Nano Letters 7 (11) (Nov. 1, 2007): 3452-3461. doi:10.1021/nl0719832.
Neeves, et al., "Composite structures for the enhancement of nonlinear-optical susceptibility," J. Opt. Soc. Am. B 6, 787-796 (1989).
Nirmal, et al., "Fluorescence intermittency in single cadmium selenide nanocrystals," Nature, 383(6603), 802, 1996.
Norton, et al., "Plasmonics Quenching and Enhancement of a Fluorescing Molecule Outside and Inside a Silver Metallic Nanoshell," IEEE Transactions on Nanotechnology 10, 1264-1274 (2011).

(56) References Cited

OTHER PUBLICATIONS

Nowak-Lovato, et al., "Targeted surface-enhanced Raman scattering nanosensors for whole-cell pH imagery," Applied Spectroscopy, 63(4), 387-395, 2009.
Nowak-Lovato, et al., "SERS nanosensors that report pH of endocytic compartments during FcεRI transit," Anal Bioanal Chem 398, 2019-2029 (2010).
Nowak-Lovato, et al., "Cells as Dynamic Laboratories: Time Lapse Raman Spectral Microscopy of Nanoparticles with Both IgE Targeting and pH-Sensing Functions," *International Journal of Analytical Chemistry* 2012, (2012).
O'donovan, et al., "Real-time imaging of neurons retrogradely and anterogradely labelled with calcium-sensitive dyes," Journal of Neuroscience Methods 46, 91-106 (1993).
Oldenburg, et al., "Surface enhanced Raman scattering in the near infrared using metal nanoshell substrates," The Journal of Chemical Physics 111, 4729-4735 (1999).
O'neal, et al., "Photo-thermal tumor ablation in mice using near infrared-absorbing nanoparticles," Cancer Letters 209, 171-176 (2004).
Ozawa, et al., "An Optical Method for Evaluating Ion Selectivity for Calcium Signaling Pathways in the Cell," Analytical Chemistry, 69(15), 3081-3085, doi:doi: 10.1021/ac9613141, 1997.
Pallaoro, et al., "Mapping Local pH in Live Cells Using Encapsulated Fluorescent SERS Nanotags," Small, Sensing Nanoparticles, 6(5), 618-622, doi:10.1002/smll.200901893, 2010.
Parak, et al., "Conjugation of DNA to Silanized Colloidal Semiconductor Nanocrystalline Quantum Dots." Chemistry of Materials 14 (5) (May 1, 2002): 2113-2119. doi:10.1021/cm0107878.
Parolini, et al.. "Microenvironmental pH Is a Key Factor for Exosome Traffic in Tumor Cells." Journal of Biological Chemistry 284 (49) (Dec. 4, 2009): 34211-34222. doi:10.1074/jbc.M109.041152.
Pastoriza-Munoz, et al. "Axial heterogeneity of intracellular pH in rat proximal convoluted tubule," J Clin Invest, 80(1), 207-215, 1987.
Pena-Rodriguez, et al., "Enhanced plasmonic behavior of incomplete nanoshells," J. Phys. Chem. C 115, 22271-22275, 2011.
Peng, et al., "Non-conformal domain decomposition methods for solving large multi-scale electromagnetic scattering problem," Proceedings of IEEE, 101(2), 298-319, 2013.
Peng, et al., "A boundary integral equation domain decomposition method for electromagnetic scattering from large and deep cavities," Journal of Computational Physics, doi: 10.1016/j.jcp.2014.10.010, 2014.
Peng, "A novel multi-trace boundary integral equation formulation for electromagnetic cavity scattering problems," IEEE Transactions on Antennas and Propagation, ISSN:0018-926X, doi:10.1109/TAP.2015.2458328, 2015.
Porumb, et al., "A calmodulin-target peptide hybrid molecule with unique calcium-binding properties," Protein Engineering, 7(1), 109-115, 1994.
Pouyssegur, et al., "Cytoplasmic pH, a key determinant of growth factor-induced DNA synthesis in quiescent fibroblasts," FEBS Letters, 190(1), 115-119, doi:doi: DOI: 10.1016/0014-5793(85)80439-7, 1985.
Pretzer, et al., "Controlled Growth of Sub-10 nm Gold Nanoparticles Using Carbon Monoxide Reductant," J. Phys. Chem. C 114, 21226-21233 (2010).
Prodan, et al., "A Hybridization Model for the Plasmon Response of Complex Nanostructures," Science 302, 419-422 (2003).
Pu, et al. "The Empirical Correlation Between Size and Two-Photon Absorption Cross Section of CdSe and CdTe Quantum Dots." Small 2 (11): 1308-1313. doi:10.1002/smll.200600157 (2006).
Rasch, et al., "Limitations on the Optical Tunability of Small Diameter Gold Nanoshells," Langmuir 25, 11777-11785 (2009).
Raschke, et al., "Gold Nanoshells Improve Single Nanoparticle Molecular Sensors." Nano Letters 4 (10) (Oct. 1, 2004): 1853-1857. doi:10.1021/nl049038q.
Ru, et al, "Principles of Surface-Enhanced Raman Spectroscopy: and related plasmonic effects," (Elsevier Science: 2008).
Sacconi, et al., "In Vivo Multiphoton Nanosurgery on Cortical Neurons." Journal of Biomedical Optics 12 (5) (Sep. 1, 2007): 050502-050502. doi:10.1117/1.2798723.
Sadik, et al., "Status of biomolecular recognition using electrochemical techniques," Biosensors and Bioelectronics, 24(9), 2749-2765, 2009.
Sasaki, et al., "Three-Dimensional pH Microprobing with an Optically-Manipulated Fluorescent Particle," Chemistry Letters, 25(2), 141-142, 1996.
Schmidt, et al., "Size-dependent two-photon excitation spectroscopy of CdSe nanocrystals," Phys. Rev. B 53, 12629-12632 (1996).
Schreiber, "Ca2+ Signaling, Intracellular pH and Cell Volume in Cell Proliferation," Journal of Membrane Biology, 205(3), 129-137-137, 2005.
Schwartz, et al., "Immunologic Release of beta-Hexosaminidase and beta-Glucuronidase from Purified Rat Serosal Mast Cells," J Immunol, 123(4), 1445-1450, 1979.
Seaton, et al., "Studies of calmodulin structure: laser Raman spectroscopy of biomolecules," XVII, Biochemistry, 22(4), 973-978, doi:doi: 10.1021/bi00273a041, 1983.
Shrode, et al., "Role of Intracellular pH in Proliferation," Transformation, and Apoptosis, Journal of Bioenergetics and Biomembranes, 29(4),393-399-399, 1997.
Salvik, "Fluorescent Probes in Cellular and Molecular Biology," 1st ed., CRC Press., 1994.
Shanmugapriya, et al., "Photoluminescence Enhancement of Nanogold Decorated CdS Quantum Dots," *J. Phys. Chem. C* 117, 12272-12278 (2013).
Smith, "Medical and biological sensors: A technical and commercial review," Sensor Review, 25(4), 241-245, 2005. Squirrel, Squirrell, J. M., Wokosin, D. L., White, J. G. & Bavister, B. D. Long-term two-photon fluorescence imaging of mammalian embryos without compromising viability. Nature Biotechnology 17, 763-767 (1999).
Stöber, et al., "Controlled growth of monodisperse silica spheres in the micron size range," Journal of Colloid and Interface Science 26, 62-69 (1968).
Stokes, et al., "Rapid Cell Mapping Using Nanoparticles and SERRS." The Analyst 134 (1): 170. doi:10.1039/b815117b. (2009).
Svoboda, et al., "In vivo dendritic calcium dynamics in neocortical pyramidal neurons," Nature 385, 161-165 (1997).
Talley, et al., "Intracellular pH Sensors Based on Surface-Enhanced Raman Scattering," Analytical Chemistry, 76(23), 7064-7068, doi:doi: 10.1021/ac049093j, 2004.
Tang, et al, "Spontaneous Organization of Single CdTe Nanoparticles into Luminescent Nanowires," Science 297, 237-240 (2002).
Tarnowski, et al., "DAPI as a useful stain for nuclear quantitation," Biotech Histochem 66, 297-302 (1991).
Tran, et al., "Use of Luminescent CdSe-ZnS Nanocrystal Bioconjugates in Quantum Dot-Based Nanosensors" physica status solidi (b) 229, 427-432 (2002).
Van Dorpe, et al., "Plasmonic Nanoparticles," ACS Nano 5, 6774-6778 (2011).
Van Ommen, et al., "Fluidization of nanopowders: a review," J. Nanopart. Res., 14, 737, 2012.
Wagenknecht, et al., "Localization of calmodulin binding sites on the ryanodine receptor from skeletal muscle by electron microscopy," Biophysical Journal, 67(6), 2286-2295, doi:doi: DOI: 10.1016/S0006-3495(94)80714-3, 1994.
Wang, et al., Antigen/Antibody Immunocomplex from CdTe Nanoparticle Bioconjugates. Nano Lett. 2, 817-822 (2002).
Wang, et al., "Measurement of two-photon absorption coefficients in colloidal semiconductor quantum dots," The 17th Annual Meeting of the IEEE Lasers and Electro-Optics Society, 2004. LEOS 2004 2, 487-488 vol. 2 (2004).
Wang, et al., "Advanced two-photon absorption devices for high speed switching and demultiplexing applications," Conference on Lasers and Electro-Optics, 2005. (CLEO) 3, 1596-1598 vol. 3 (2005).
Wang, et al., "Surface-plasmon enhanced fluorescence in CdSe/ZnS semiconductor quantum dots," Conference on Lasers and Electro-

(56) References Cited

OTHER PUBLICATIONS

Optics, 2009 and 2009 Conference on Quantum electronics and Laser Science Conference. CLEO/QELS 2009 1-2 (2009).

Wang, et al., "Maximization of nonlinear fluorescence from ultrasmall (<2 nm) semiconductor quantum dots to be used for deep tissue imaging," Journal of the Optical Society of America B 26, 2161 (2009).

Wang, et al., "Enhancement of Two-Photon Absorption-Induced Florescence in Semiconductor Quantum Dots by Gold Nanoparticles," Nonlinear Optics: Materials, Fundamentals and Applications NME4 (2009).

Wang, "Nonlinear Optics in Quantum-Confined and Surface_ Plasmon Structures," https://repository.unm.edu/handle/1928/10916 (2010). Electrical and Computer Engineering.

Wang, et al., "Refractive index and dielectric constant transition of ultra-thin gold from duster to Film," Opt. Express 18, 24859-24867 (2010).

Wang, et al., "Apparatus and Methods Using Nontoxic Synthetic Luminophores," U.S. Appl. No. 13/099,217, filed May 2, 2011.

Wang, et al., "Amorphous nanoshell formed through random growth and related plasmonic behaviors," Chem. Phys. Letts, 610-611, 278-283, 2014.

Williams, et al., "Multiphoton microscopy in biological research," Current Opinion in Chemical Biology 5, 603-608 (2001).

Xia, et al., "Engineering sub-100 nm multi-layer nanoshells," Nanotechnology 17, 5435-5440 (2006).

Xiao, et al., "Dynamics and mechanisms of quantum dot nanoparticle cellular uptake," Journal of Nanobiotechnology, 8(1), 13, doi:10.1186/1477-3155-8-13, 2010.

Xu, et al., "Measurement of two-photon excitation cross sections of molecular fluorophores with data from 690 to 1050 nm," J. Opt. Soc. Am. B 13, 481-491 (1996).

Xu, "Multilayered metal core-shell nanostructures for inducing a large and tunable local optical field," Phys. Rev. B 72, 073405 (2005).

Xu, et al., "Cell Nucleus Penetration by Quantum Dots Induced by Nuclear Staining Organic Fluorophore and UV-Irradiation," Advanced Materials 20 (18): 3468-3473. doi:10.1002/adma.200703238 (2008).

Yaghini, et al., "Quantum dots and their potential biomedical applications in photosensitization for photodynamic therapy," Nanomedicine 4, 353-363 (2009).

Yang, et al., "Folate receptor-targeted quantum dot liposomes as fluorescence probes," Journal of Drug Targeting, 17(7), 502-511, 2009.

Yong, et al., "Multiplex Imaging of Pancreatic Cancer Cells by Using Functionalized Quantum Rods." Advanced Materials 20 (8): 1412-1417. doi:10.1002/adma.200702462 (2008).

Yuan, et al., "Plasmonic Nanoprobes for Intracellular Sensing and Imaging." Analytical and Bioanalytical Chemistry 405 (19) (Jul. 1): 6165-6180. doi:10.1007/s00216-013-6975-1 (2013).

Yukawa, et al., "Quantum dots for labeling adipose tissue-derived stem cells," Cell Transplant, 18(5), 591-599, 2009.

Yu-Ming, et al., "Light scattering by arrays of gold nanospheres and nanoellipsoids," in Electromagnetic Compatibility and 19th International Zurich Symposium on Electromagnetic Compatibility, 2008. APEMC 2008. Asia-Pacific Symposium on, pp. 586-589. [Online] Available from: 10.1109/APEMC.2008.4559943, 2008.

Zhang, et al., "The Dynamic Control of Kiss-And-Run and Vesicular Reuse Probed with Single Nanoparticles," Science, 323(5920), 1448-1453, 2009.

Ziolkowski, "Metamaterial-based source and scattering enhancements: From microwave to optical frequencies," Opto-Electronics Review, 14(3), 167-177-177, 2006.

"Quantum dot", Wikipedia, (URL: https://en.wikipedia.org/wiki/Quantum_dot), retrieved Aug. 5, 2019, 28 pages.

Anonymous, "Quantum Dot", Science Daily, accessed Oct. 15, 2020, 5 pages.

Anonymous, "Quantum dot" Wikipedia, accessed Oct. 15, 2020, 27 pages.

\* cited by examiner

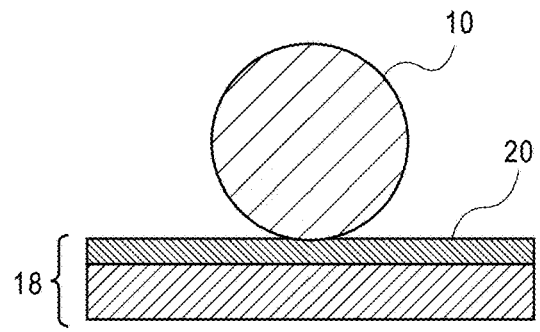
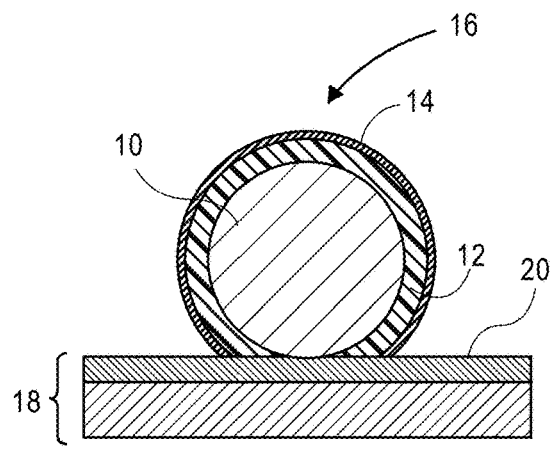
FIG. 1A  FIG. 1B
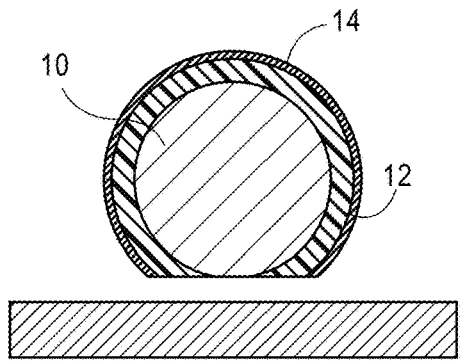
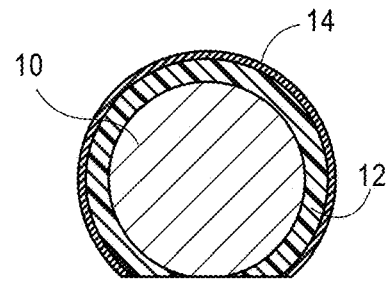
FIG. 1C  FIG. 1D
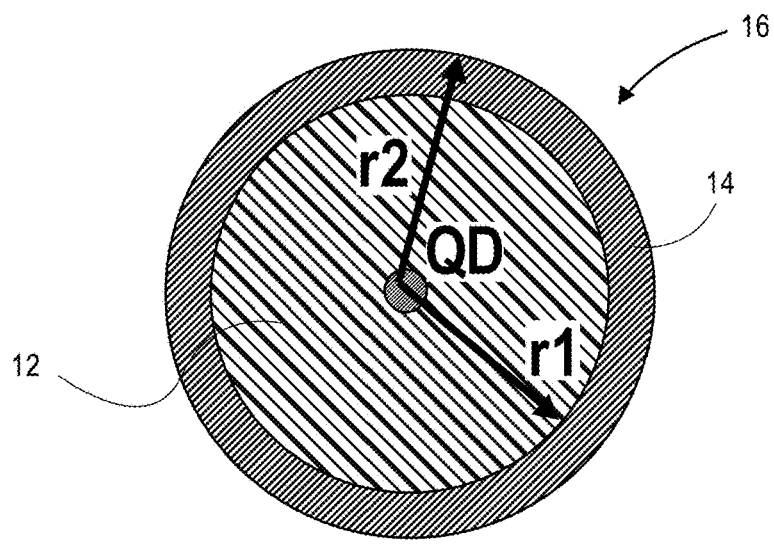
FIG. 2

PLASMONIC NANOPARTICLES, METHODS OF MAKING PLASMONIC NANOPARTICLES AND SENSORS MADE THEREFROM

PRIORITY DOCUMENTS

The present disclosure claims priority benefit to U.S. Provisional Application No. 62/415,953, filed on Nov. 1, 2016, the disclosure of which is incorporated herein by reference in its entirety.

DETAILED DESCRIPTION

Field of the Disclosure

The present disclosure relates to quantum dots and in particular to plasmonic nanoparticles as nonlinear optical materials for sensing applications.

Background

High-efficiency light-absorbing and light-emitting materials and related composite material nanostructures can be usefully employed in a large range of photonic devices and systems, ranging from solar cells and high-efficiency detectors to advanced light emitter-based applications, including bio-imaging sensors and systems based on multiphoton light absorption and single photon emission. As a case in point, two-photon absorption-induced fluorescence (TPAF) in semiconductor quantum dots has been demonstrated as a highly-effective nonlinear optical phenomenon for several bio-imaging applications—particularly for deep-tissue imaging—and for photodynamic therapy. See Larson, Daniel R., et al., "Water-Soluble Quantum Dots for Multiphoton Fluorescence Imaging in Vivo," Science 300 (5624) (May 30): 1434-1436; and Wang, L. et al., "Maximization of nonlinear fluorescence from ultrasmall ($\leq 2$ nm) semiconductor quantum dots to be used for deep tissue imaging," Journal of the Optical Society of America B 26, 2161 (2009). In the latter case, focusing intense near-infrared radiation (NIR) in cancer tissue (at a wavelength in the tissue optical transparency window of 600-1300 nm) results in deep tissue penetration of the radiation, followed by selective destruction of malignant cells via efficient TPAF-induced cytotoxic reactive oxygen species (ROS) generation. See Yaghini, E., et al., Quantum dots and their potential biomedical applications in photosensitization for photodynamic therapy. Nanomedicine 4, 353-363 (2009). Additional targeting of specific tissue can also be achieved by functionalizing the TPAF nanoparticles with biomolecules to cause increased accumulation in the target tissue, both for photodynamic therapy and for imaging applications.

With regard to nanostructures for TPAF-based bioimaging, there has been a long-standing need for non-photobleaching and nontoxic TPAF materials for ultrahigh brightness fluorophores. Because of their numerous advantages over other fluorophores, including: (a) broad absorption spectra and readily tunable emission, (b) high quantum yields, (c) relatively high photochemical stability, and (d) their relatively large two-photon absorption cross sections, semiconductor quantum dots (QDs) have attracted significant attention as TPAF nanoparticle labels. Nevertheless, the cytotoxicity of several elements (such as cadmium) contained in QDs—along with the need for higher brightness nanoparticles of sub-100 nm dimensions—has created an unresolved need for new non-toxic ultrabright nanoparticle emitters for TPAF applications, particularly for in vivo clinical use.

Moreover, there has been a growing need for nanoparticle sensors in recent years for numerous biosensing applications, including for the detailed study of intracellular and extracellular processes in various cells and tissue structures. See Clark, H. A., et al., "Optical Nanosensors for Chemical Analysis inside Single Living Cells. 1. Fabrication, Characterization, and Methods for Intracellular Delivery of PEBBLE Sensors, Analytical Chemistry", 71(21), 4831-4836; Smith, J. P.: Medical and biological sensors: A technical and commercial review, Sensor Review, 25(4), 241-245, 2005; and Lee, Y. K., et al., Nanoparticle PEBBLE Sensors in Live Cells and In Vivo, Annual Review of Analytical Chemistry, 2(1), 57-76. A major advance has involved the use of "optical" nanoparticles and—all-optical techniques—for the measurement of ion concentrations in live cells, including the mapping of local pH in a real-time non-invasive manner. See Pallaoro, A., et al., Mapping Local pH in Live Cells Using Encapsulated Fluorescent SERS Nanotags, Small, 6(5), 618-622; Nowak-Lovato, K. et al., "Targeted surface-enhanced Raman scattering nanosensors for whole-cell pH imagery, Applied Spectroscopy, 63(4), 387-395, 2009; Nowak-Lovato, K. L., "SERS nanosensors that report pH of endocytic compartments during FcεRI transit," Anal Bioanal Chem 398, 2019-2029 (2010). The need for nano-sized particles for such applications stems largely from their ability to be inserted in specific cells and organelles, as opposed to a need for sub-micron spatial resolution.

Even though, at first glance, plasmonic field enhancements outside the metallic shell nanoparticles appear fairly obvious, the physics of the plasmonic enhancement of the fields inside the metallic nanoparticles is not as obvious. Since the thicknesses of the metallic shells are much less than the skin depths in these materials, attenuation of the optical frequencies of interest is not a significant issue. As such, the behaviours of the strong surface plasmon resonances (SPRs) in these nanoparticles, and spatial distribution of the fields—both inside and outside these nanoparticles—are best attributed to relatively complex but somewhat intangible SPR interactions; these are most simply and most accurately describable by simple Mie scattering theory. The primary focus of past work has been on the electric field external to such multilayered nanoparticles. Enderlein et al., has hypothesized that the external shell acts somewhat like a nanocavity for the field enhancement, while Liaw et al., has proposed that the net effect of the Mie scattering is similar to a focusing of the irradiated light into the center of the nanoshelled structures. See Kerker, M. et al., "Elastic scattering, absorption, and surface-enhanced Raman scattering by concentric spheres comprised of a metallic and a dielectric region," Phys. Rev. B 26, 4052-4063 (1982); Jackson, J. B., et al., "Controlling the surface enhanced Raman effect via the nanoshell geometry" Applied Physics Letters 82, 257-259 (2003); Prodan, E. et al., "Hybridization Model for the Plasmon Response of Complex Nanostructures" Science 302, 419-422 (2003); Liaw, J.-W. et al., "Bi-dipole emission via plasmon modes of Au/Ag nanoshell", *Journal of Quantitative Spectroscopy and Radiative Transfer* (2012); and Enderlein, J., "Spectral properties of a fluorescing molecule within a spherical metallic nanocavity", Phys. Chem. Chem. Phys. 4, 2780-2786 (2002). However, none of these researchers elucidate the physics of the cavity-like behavior or the focusing behavior in any rigorous or tangible manner, such as by predicting the spectral location of the resonances or the degree of focusing as a function of nanocavity or nanoshell dimensions.

It has been further proposed that the concepts of "optical condensers" and of "collective coupling of surface plasmons between the multiple metal shells" could cause multilayered metal shells to act as more "effective optical condensers to focus the incident light toward the geometric center multiplicatively", but focused only on large field enhancements in multilayered structures with metallic cores. Large field enhancements external to large-shell-number multilayered nanoshell structures in such "nanolayered alternating metal-dielectric probes" ("nano-LAMPs") have been predicted for Surface Enhanced Raman Specroscopy ("SERS") applications. Mie theory has been used to analyze alternating silica-silver shelled structures with a silver core in a vacuum environment, and calculated an intensity enhancement of $1.2 \times 10^5$ in a 1 nm thick innermost silica shell for a structure with a silver core and 8 alternating silica-silver shells (4 metal shells). See Xu, H., "Multilayered metal core-shell nanostructures for inducing a large and tunable local optical field," Phys. Rev. B 72, 073405 (2005) and Kodali, A. K., et al., "Optimally designed nanolayered metal-dielectric particles as probes for massively multiplexed and ultrasensitive molecular assays," PNAS 107, 13620-13625 (2010).

Most previous pH nanosensors have been based on fluorescent organic dyes, whose emission intensities change with surrounding pH values. For example, 4-Methylumbelliferyl acetate (which can detect pH in the range of 6.7-7.3) has been used to measure the intracellular pH in rat proximal convoluted tubule, and Oregon Green 514 (which is pH-insensitive fluorescence at pH>6) has been used for lysosomal pH measurements in murine macrophages. See Pastoriza-Munoz, E., et al., "Axial heterogeneity of intracellular pH in rat proximal convoluted tubule", J Clin Invest, 80(1), 207-215, 1987; Ji, J., et al., "Synthesis and application of submicrometer fluorescence sensing particles for lysosomal pH measurements in murine macrophages," Analytical Chemistry, 72(15), 3497-3503, 2000; Geisow, M. J., "Fluorescein conjugates as indicators of subcellular pH: A critical evaluation," Experimental Cell Research, 150(1), 29-35 (1984). Even though fluorescence intensity changes are easy to detect, they tend to give inaccuracies in absolute values of pH. Moreover, organic dye-based fluorescence tags suffer from numerous problems, such as photobleaching, small two-photon absorption coefficients (TPA coefficients on the order of just a few Goeppert-Mayer units), limitations on laser excitation wavelengths, and high susceptibility of the fluorescence intensity changes to environmental changes. SERS-based nanosensors can alleviate the problem of the susceptibility to spurious environmental changes by providing a well-defined "signature" spectral shift. Hu, J., et al., "Surface-enhanced Raman spectroscopy study on the structure changes of 4-mercaptopyridine adsorbed on silver substrates and silver colloids, Spectrochimica Acta Part A: Molecular and Biomolecular Spectroscopy, 58, 2827-2834, (2002).

SERS-based pH sensors have been developed for pH values (in the range of 6-8) using 50-80 nm silver nanoparticle clusters functionalized with 4-mercaptobenzoic acid. Talley, C. E., et al., "Intracellular pH Sensors Based on Surface-Enhanced Raman Scattering," Analytical Chemistry, 76(23), 7064-7068 (2004). Improvement in the pH sensitivity of such sensors was demonstrated by using nanoshells, which have larger field enhancement factors; an average accuracy of +/−0.1 pH units was demonstrated. Bishnoi, S. W., et al., All-Optical Nanoscale pH Meter, Nano Letters, 6(8), 1687-1692 (2006). pH-sensitive dyes have been attached as fluorophores on silver colloids to make SERS nanotags to map the local pH value inside living HeLa cells. Pallaoro, A. et al., "Mapping Local pH in Live Cells Using Encapsulated Fluorescent SERS Nanotags, Small, 6(5), 618-622 (2010). Recently, B. Wilson, Kirk Rector, Nowak-Lowato, and their colleagues at LANL published the first study of an FcεRI (IgE) receptor-targeted SERS pH-sensitive nanosensor; whole, live cell hyperspectral pH-calibrated images were demonstrated. See Nowak-Lovato, K. et al., "Targeted surface-enhanced Raman scattering nanosensors for whole-cell pH imagery," Applied Spectroscopy, 63(4), 387-395 (2009). Subsequently, these researchers demonstrated the use of such targeted SERS pH nanosensors to record the dynamic response of live cells to thermal or drug-based stimuli by measuring the distribution of pH values along the endocytosis pathway. Nowak-Lovato, K. L., et al., "SERS nanosensors that report pH of endocytic compartments during FcεRI transit," Anal Bioanal Chem 398, 2019-2029 (2010).

In a recent study, Ji et al. reported synthesis of quantum dot structures. See Ji B., et al., Nature Nanotechnology, vol. 10, February 2015, DOI: 10.1038/NNANO.2014.298. However, these authors have not focused on the issue of large electric field enhancements (EFEs). Unfortunately, the liquid phase routes used exclusively in the work of Ji et al. do not allow the fabrication of ultrahigh film quality and uniformity at sub-10 nm dimensions, or the use of other much more desirable dielectrics, such as titania, which are beneficial for the large EFEs needed for various end-use applications. Klopfer, M. et al., "Plasmonic Quantum Dots for Nonlinear Optical Applications," Nonlinear Optics: Materials, Fundamentals and Applications NThB3 (2011); Klopfer, M. et al., "Plasmonic quantum dots for nonlinear optical applications," Opt. Mater. Express 1, 1353-1366 (2011). This is because the much faster hydrolysis rates of the Ti based alkoxides lead inevitably to highly non-uniform and uncontrolled film growth at sub-10 nm dimensions. Furthermore, the two step metal deposition approach used by Ji et al. leads to irregular gold surface layers, whose thickness cannot be precisely controlled.

Atomic layer deposition (ALD) is a technology for fabricating conformal layers of precisely controlled thickness on substrates of almost any shape and size. The ALD process involves a series of chemical reactions of the type A-B where step A must be completed and the precursor flushed out before reactant B is introduced. This ensures that only one monolayer (or less—depending on the surface chemistry of the substrate) is deposited in each cycle. Controlling the number of cycles allows precise control over coating thickness.

There are many examples of sub-10 nm ultra-thin films prepared by the ALD deposition of various oxide (e.g. $Al_2O_3$, $TiO_2$, $SiO_2$ etc.) and metals (e.g. Pt, Pd, Ru, Ir etc. A recent review of the parameters and precursors have been reported by Hamalainen et al., which provides an excellent summary of previous work. See Hamalainen, J. et al., Chem. Mater. 2014, 26, 786-801. Also see George, Steven M., Chem. Rev. 2010, 110, 111-131; Bent, Stacey F. et al., Materials Today Volume 17, Number 5 Jun. 2014; Aaltonen, Titta, "Atomic Layer Deposition of Noble Metal Thin Films," Academic Dissertation, Dept. of Chemistry, University of Helsinki, 2005. While deposition of Au and Ag was reported to be challenging due to lack of suitable precursors, the recent work of Coyle et al. has demonstrated precursors for both Au and Ag for deposition via ALD. Coyle, Jason P. et al., Chem. Mater. 2013, 25, 4566-4573.

While originally developed for the semi-conductor industry for flat samples, with proper handling of the material, ALD is also known for coating powders. ALD systems designed to handle powders are known in the art. For example, ALD chambers designed to allow continuous agitation of the particles during the ALD process can ensure conformal coating of powders. Approaches that involve fluidization of particles for ALD are known. See, e.g., L. F. Hakim et al., Powder Technology 160 (2005) 149-160 and J. R. Van Ommen, J. Nanopart Res (2012) 14:737, the disclosures of both of which are incorporated herein by reference in their entirety. The literature shows that particles as small as 12 nm in diameter have been successfully coated using ALD.

Studies of related subject matter have been reported in a number of other articles. These articles include: 1) Wang, L., "Nonlinear Optics in Quantum-Confined and Surface_Plasmon Structures," https://repository.unm.edu/handle/1928/10916(2010). Electrical and Computer Engineering; 2) Peng, Z. et al., "Non-conformal domain decomposition methods for solving large multi-scale electromagnetic scattering problem," Proceedings of IEEE, 101(2), 298-319, 2013; 3) Peng, Z. et al., "A boundary integral equation domain decomposition method for electromagnetic scattering from large and deep cavities," Journal of Computational Physics, doi: 10.1016/j.jcp.2014.10.010, 2014; 4) Stöber, W. et al., "Controlled growth of monodisperse silica spheres in the micron size range," Journal of Colloid and Interface Science 26, 62-69 (1968); 5) Kah, James, et al., "Synthesis of Gold Nanoshells Based on the Depositionprecipitation Process" Gold Bulletin 41 (1): 23-36 (2008) doi:10.1007/BF03215620; and 6) Koole, Rolf et al., "On the Incorporation Mechanism of Hydrophobic Quantum Dots in Silica Spheres by a Reverse Microemulsion Method." Chemistry of Materials 20 (7) (April 1): 2503-2512 (2008) doi: 10.1021/cm703348y.

There is a need for non-toxic plasmonic nanoparticles for high spatial resolution (sub-100 nm) TPAF imaging and other biological sensing applications and methods of making and using them.

SUMMARY

An embodiment of the present disclosure is directed to a method of making free-standing ALD-coated plasmonic nanoparticles. The method comprises providing a plurality of semiconductor quantum dots. One or more conformal layers of dielectric material are deposited over the quantum dots to form dielectric-coated quantum dots. A conformal metallic nanoshell is deposited over the dielectric-coated quantum dots to form plasmonic nanoparticles. At least one layer chosen from i) the conformal layers of dielectric material and ii) the conformal metallic nanoshell is deposited using a vapor phase atomic layer deposition (ALD) process.

Another embodiment of the present disclosure is directed to a plasmonic nanoparticle. The plasmonic nanoparticle comprises a semiconductor quantum dot. At least one conformal layer of dielectric insulating material is disposed over the semiconductor quantum dot. A conformal metallic nanoshell is disposed over the at least one dielectric insulating layer, such that one or more of the conformal layers of dielectric insulating material are disposed between the semiconductor quantum dot and the metallic nanoshell. At least one layer chosen from i) the conformal layers of dielectric material and ii) the conformal metallic nanoshell is deposited using vapor phase atomic layer deposition (ALD).

Yet another embodiment of the present disclosure is directed to a nanosensor system. The nanosensor system comprises an illumination source; an optical signal detector; and a plasmonic nanoparticle. The plasmonic nanoparticle comprises: a semiconductor quantum dot; at least one conformal layer of dielectric insulating material disposed over the semiconductor quantum dot; and a conformal metallic nanoshell disposed over the at least one dielectric insulating layer, such that one or more of the conformal layers of dielectric insulating material are disposed between the semiconductor quantum dot and the metallic nanoshell. At least one layer chosen from i) the conformal layers of dielectric material and ii) the conformal metallic nanoshell is deposited using vapor phase atomic layer deposition (ALD).

The plasmonic nanoparticles, methods of making the plasmonic nanoparticles and/or the sensors of the present disclosure have one or more of the following benefits: the ability to form nanoparticle-based plasmonic nanosensors for high spatial resolution (sub-100 nm) TPAF imaging and other biological sensing applications; the ability to form composite plasmonic nanosensors comprising fully-enclosed metal and insulator-encapsulated semiconductor quantum dots; the ability to employ a large range of insulator and metallic materials for uniform, non-uniform, continuous and discontinuous film geometries; the ability to fabricate and/or optimize nonlinear optical nanometric luminophores; the ability to fabricate plasmonic quantum dots having internal EFEs (electric field enhancements) higher than 1, such as 2, 5 or 10 or higher; the ability to provide appropriately targeted PQD nanoparticles for bio sensing applications; the ability to form and/or optimize sub-100 nm optical nanosensors (SERS nanotags) capable of allowing precise measurements of a variety of ions of biological interest, with a spatial accuracy on the order of, for example, 1 micron; the ability to provide plasmonic nanosensors for ultraprecise pH sensing, with a resolution of, for example, better than 100 nm; and the ability to provide pH nanosensors for pH-sensing and/or Ca ion sensing that may be employed, for example, in the study of the fundamentals of neuronal communication via measurement of pH-sensitive synaptic processes.

It is to be understood that both the foregoing general description and the following detailed description are exemplary and explanatory only and are not restrictive of the present teachings, as claimed.

BRIEF DESCRIPTION OF THE DRAWINGS

The accompanying drawings, which are incorporated in and constitute a part of this specification, illustrate embodiments of the present teachings and together with the description, serve to explain the principles of the present teachings.

FIG. 1A illustrates semiconductor quantum dots dispersed on a support comprising a sacrificial material, according to an embodiment of the present disclosure.

FIG. 1B illustrates conformal layers deposited over the quantum dots, according to an embodiment of the present disclosure.

FIG. 1C illustrates dissolving the sacrificial material of the support, according to an embodiment of the present disclosure.

FIG. 1D illustrates that the resulting coated QDs of FIG. 1B can be separated from the sacrificial support, according to an embodiment of the present disclosure.

FIG. 2 illustrates a semiconductor quantum dot coated with a dielectric material and a metallic shell, according to an embodiment of the present disclosure.

Figure 3:
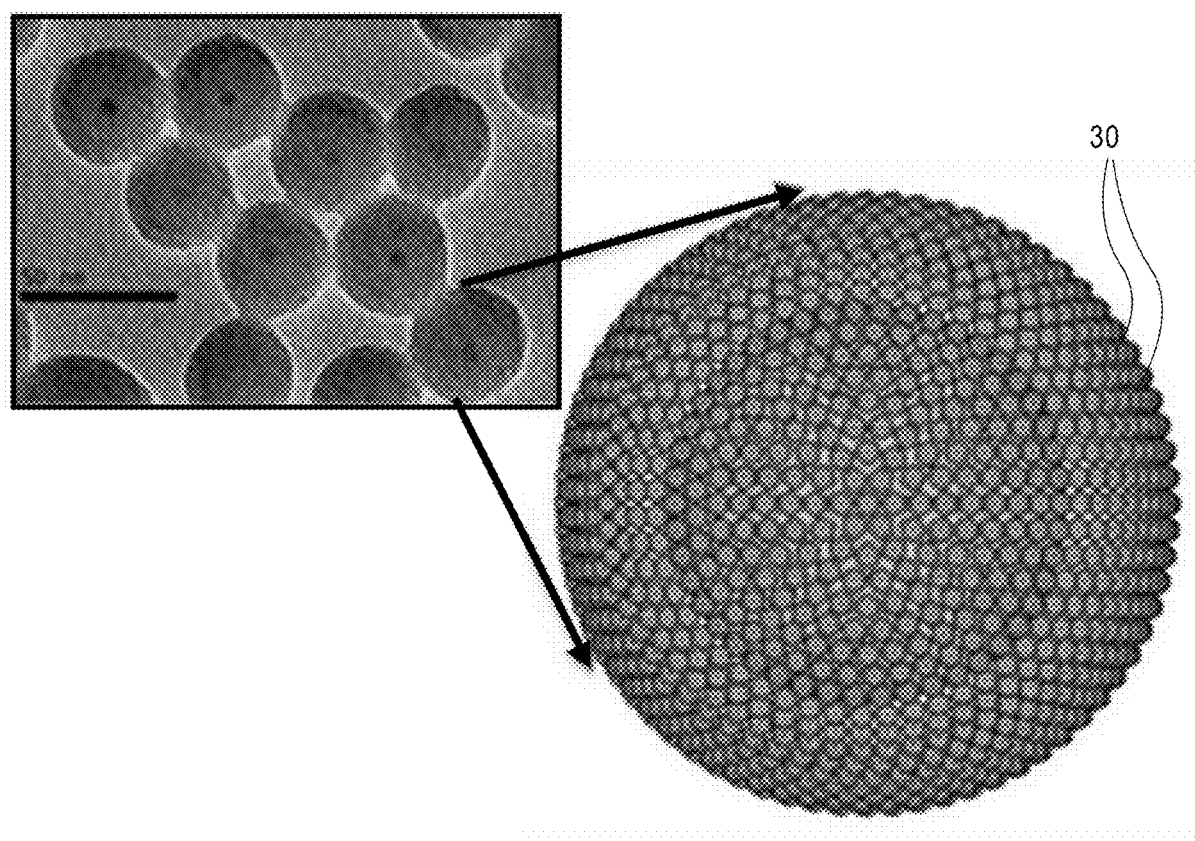
FIG. 3 illustrates a metallic nanoshell covering a quantum dot, as described herein, the metallic nanoshell comprising an array of metallic dots, according to an embodiment of the present disclosure.

It should be noted that some details of the figure have been simplified and are drawn to facilitate understanding of the embodiments rather than to maintain strict structural accuracy, detail, and scale.

DESCRIPTION OF THE EMBODIMENTS

Reference will now be made in detail to embodiments of the present teachings, examples of which are illustrated in the accompanying drawings. In the drawings, like reference numerals have been used throughout to designate identical elements. In the following description, reference is made to the accompanying drawing that forms a part thereof, and in which is shown by way of illustration a specific exemplary embodiment in which the present teachings may be practiced. The following description is, therefore, merely exemplary.

An embodiment of the present disclosure is directed to a method of making free-standing ALD-coated plasmonic nanoparticles. Referring to FIG. 1A, the method comprises providing a plurality of semiconductor quantum dots (QDs) 10 and other optionally embedded fluorophores such as organic dyes. One or more conformal layers of dielectric material 12 are deposited over the quantum dots 10 to form dielectric-coated quantum dots, as illustrated in FIG. 1B. A conformal metallic nanoshell 14 is deposited over the dielectric-coated quantum dots to form plasmonic nanoparticles 16. At least one layer chosen from i) the conformal layers of dielectric material and ii) the conformal metallic nanoshell is deposited using a vapor phase atomic layer deposition (ALD) process.

In an embodiment, the semiconductor quantum dots are optionally dispersed on a support 18 comprising a sacrificial material 20, as illustrated in FIG. 1A. Examples of the sacrificial material include carbon or organic materials that can be etched by oxygen plasma, UV irradiation, or highly oxidization solvent; metals or metal oxides or other inorganic materials that can be easily removed by acids or bases, e.g. electroplated copper, which can be dissolved by an acid, such as $HNO_3$; polymers or salts or other materials that can be dissolved by using solvent, e.g. PMMA that can be rinsed off using acetone, NaCl salt that can be rinsed off by water; or any suitable volatile material that will be burned out or vaporized at elevated temperatures. Depending on the chemistry of the sacrificial material surface, the ALD may or may not deposit a film on the sacrificial material. In an embodiment, layer 20 has a hydrophobic surface (e.g., carbon) so that ALD will not occur on the sacrificial material.

ALD can be employed to provide highly conformal dielectric and metal coatings of the QDs. The ALD technique is particularly beneficial for forming the plasmonic particles of the present disclosure because it allows the thickness of the coating to be precisely controlled by varying the number of ALD cycles. In addition, the ALD can allow for a variety of materials to be used as coatings that may not otherwise be easily coated onto the QDs. For example, titania has a higher refractive index than silica, which is desirable for plasmonic nanoparticles of the present disclosure. However sol-gel synthesis of titania is more difficult due to the higher reactivity of the alkoxide precursor. According to an embodiment of this disclosure, ALD is used to provide the desired conformal dielectric coatings, such as titania, over the QDs.

The ALD process comprises: a) optionally placing the semiconductor quantum dots on a sacrificial support under vacuum at a temperature in the range of 80° C. to 250° C.; b) forming a chemisorbed monolayer of a first reactant on at least a portion of a surface of the semiconductor quantum dots; c) forming an atomic layer of a material over the semiconductor quantum dots by reacting a second reactant with the chemisorbed monolayer of the first reactant; and d) repeating steps b) and c) to achieve a desired layer thickness. Between each step a), b), c) and d), a vacuum may be applied and optionally an inert gas can be pumped through the ALD vacuum chamber to remove an excess of first reactant, second reactant, and reaction byproducts, and any weakly bonded physi-sorption layer on the surface of the quantum dot.

Any suitable number or type of reactant gases can be employed depending on the desired composition of the layer to be deposited by the ALD process. For example, the process can include adding a third reactant and optionally a fourth reactant to form a coating with ternary or quaternary compositions, respectively. If the dielectric material to be deposited is alumina, ($Al_2O_3$), the first reactant in the ALD process can be trimethyl aluminum (TMAl) and the second reactant can be water. In another example where the dielectric material is titania (TiO$_2$) the first reactant is titanium tetrachloride (TCl$_4$) and the second reactant is water. In and example where the layer(s) to be deposited by ALD include the conformal metallic nanoshell, the nanoshell can comprise palladium, the first reactant is Pd(hfac)$_2$ and the second reactant is hydrogen. Various other films and known ALD precursors for making the films are shown in Table 1 below. The vapor phase (ALD) techniques will not only allow a larger choice of high quality ultrathin (<10 nm thickness) dielectric (such as titania) and metal films, but also enable the possibility of getting unprecedented film uniformity and thickness control for both the dielectric and metal film layers.

TABLE 1

| ALD product | ALD precursors | References |
|---|---|---|
| Al$_2$O$_3$ | TMAl + H$_2$O | [George, 2010[1]; Bent, 2014[2]] |
| TiO$_2$ | TiCl$_4$ + H$_2$O | [George, 2010[1]; Bent, 2014[2]] |
| SiO$_2$ | TMOS + H$_2$O | [George, 2010[1]; Bent, 2014[2]] |
| ZnO | DMZ + H$_2$O | [George, 2010[1]; Bent, 2014[2]] |
| Pt | MeCpPtMe$_3$ + O$_2$ or H$_2$ at 200-350° C. | [Aaltonen, 2005][3] |
| Pd | Pd(hfac)$_2$ + H$_2$ at 80-130° C. | [Aaltonen, 2005][3] |
| Ru | RuCp$_2$ + O$_2$ at 225-275° C. | [Aaltonen, 2005][3] |
| Ir | Ir(acac)$_3$ + O$_2$ 225-400° C. | [Aaltonen, 2005][3] |
| Au | Au Iminopyrrolidinates, plasma ALD | [Coyle, 2014][4] |
| Ag | Ag Iminopyrrolidinates, plasma ALD | [Coyle, 2014[4]; Hämäläinen, 2014][5] |

[1]George, Steven M., Chem. Rev. 2010, 110, 111-131, the disclosure of which is incorporated herein by reference in its entirety.
[2]Bent, Stacey F. et al., Materials Today Volume 17, Number 5 June 2014, the disclosure of which is incorporated herein by reference in its entirety.
[3]Aaltonen, Titta, "Atomic Layer Deposition of Noble Metal Thin Films," Academic Dissertation, Dept. of Chemistry, University of Helsinki, 2005, the disclosure of which is incorporated herein by reference in its entirety.
[4]Coyle, Jason P. et al., Chem. Mater. 2013, 25, 1132-1138, the disclosure of which is incorporated herein by reference in its entirety.
[5]Hämäläinen, J. et al., Chem. Mater. 2014, 26, 786-801, the disclosure of which is incorporated herein by reference in its entirety.

The ALD technique is very flexible, but a major challenge involves the handling of QD nanoparticles, which are generally less than 6 nm in diameter, such as less than 3 nm in diameter, during the ALD coating process. According to an embodiment of the present disclosure, a two-step approach can be employed to allow ALD coating of QDs. In step one, the method includes coating the semiconductor dots prior to depositing the one or more conformal layers of dielectric material. For example, the semiconductor quantum dots can be coated with silica using a liquid phase sol-gel method to form silica-coated quantum dots having a size suitable for vapor phase atomic layer deposition (ALD). Such liquid phase techniques are generally well known for depositing silica and can preserve the fluorescence of the QDs after the silica coating. The liquid phase coated QD structures are of a size that allows handling via ALD. For example, the liquid phase coated particles can have a diameter ranging from about 10 nm to about 200 nm, such as about 15 nm to about 150 nm, such as about 20 nm to about 100 nm. In step two, the ALD dielectric and/or metal nanoshell layers can be deposited over free flowing silica-coated quantum dots using the above described vapor phase ALD process.

Following the deposition of the dielectric and/or the metallic nanoshell, the resulting coated QDs can be separated from the sacrificial support, such as by etching or dissolving the sacrificial material 20 of the support, as shown in FIGS. 1C and 1D. Then the coated QDs can be further processes in any desired manner, such as to purify or otherwise clean the coated QDs. The semiconductor quantum dot 10 of the resulting plasmonic nanoparticles 16 may be partially encapsulated, as shown in FIG. 1D. Alternatively, the semiconductor quantum dot 10 may be fully encapsulated. For instance, the deposition of the dielectric and/or the metallic nanoshell can be repeated after removing the sacrificial layer 20 in order to fully encapsulate the semiconductor quantum dot 10. In one embodiment, the sacrificial material 20 can be removed after ALD of the dielectric material 12, followed by a second ALD of dielectric to fully encapsulate the quantum dot 10 in the dielectric material 12. A similar, two-step ALD process can then be carried out to deposit metallic nanoshell 14 using ALD so as to fully encapsulate the dielectric material 12 in the metallic nanoshell 14. Any other suitable process can also be employed for fully or partially encapsulating the semiconductor quantum dot 10 using ALD.

An embodiment of the present disclosure is also directed to plasmonic nanoparticles. The nanoparticles comprise a semiconductor quantum dot 10, as shown in FIG. 2. At least one conformal layer of dielectric material 12 is disposed over the semiconductor quantum dot. A conformal metallic nanoshell is disposed over the at least one conformal layer of dielectric material 12, such that one or more of the conformal layers of dielectric insulating material are between the semiconductor quantum dot 10 and the metallic nanoshell 14. At least one layer chosen from i) the conformal layers of dielectric material and ii) the conformal metallic nanoshell is deposited using vapor phase atomic layer deposition (ALD).

Any suitable semiconductor quantum dots can be employed in the plasmonic nanoparticles of the present disclosure. For example, the semiconductor quantum dots can comprise at least one material selected from the compositions of CdSe/ZnS, CdSe/CdS and ZnSe/ZnS.

In an embodiment, the semiconductor quantum dot is a fluorophore and the plasmonic nanoparticle further comprising a second fluorophore. For instance, the second fluorophore can be selected from the group consisting of semiconductor nanoparticles, such as any of the quantum dots described herein, or organic dyes such as fluorescein or rhodamine.

The layer of dielectric material 12 (sometimes referred to herein as the "dielectric layer") can comprise any suitable material that has the desired permittivity and that can be formed in a suitably conformal layer that does not inhibit the function of the plasmonic nanoparticle. In an embodiment, the at least one dielectric insulating layer comprises at least one material chosen from the compounds of silica, titania and alumina. The dielectric layer 12 can be deposited to be sufficiently thick so as to minimize nonradiative decay and improve the plasmonic resonant enhancement of the plasmonic nanoparticle. The total thickness of the dielectric layer 12 (including the combined thickness of the ALD deposited dielectric and any optional dielectric deposited by liquid phase techniques) can range, for example, from about 3 nm to about 100 nm, such as about 5 nm to about 50 nm, such as about 10 nm to about 20 nm.

The metallic nanoshell can comprise any suitable metals. In an embodiment, the metallic nanoshell comprises one or more metals selected from gold, silver, platinum, palladium, aluminum, copper, and nickel. In general, the thickness of the metal nanoshell 14 can range, for example, from about 0.1 nm to about 15 nm, such as about 0.2 to about 8 nm, such as about 0.2 to about 6 nm or about 1 nm to about 5 nm.

In an embodiment, the metallic nanoshell is a multilayered metallic nanoshell, wherein each layer has a unique composition. For example, the metallic nanoshell can include two or more layers chosen from gold, silver, platinum, palladium, aluminum, copper, and nickel.

Figure 4A:
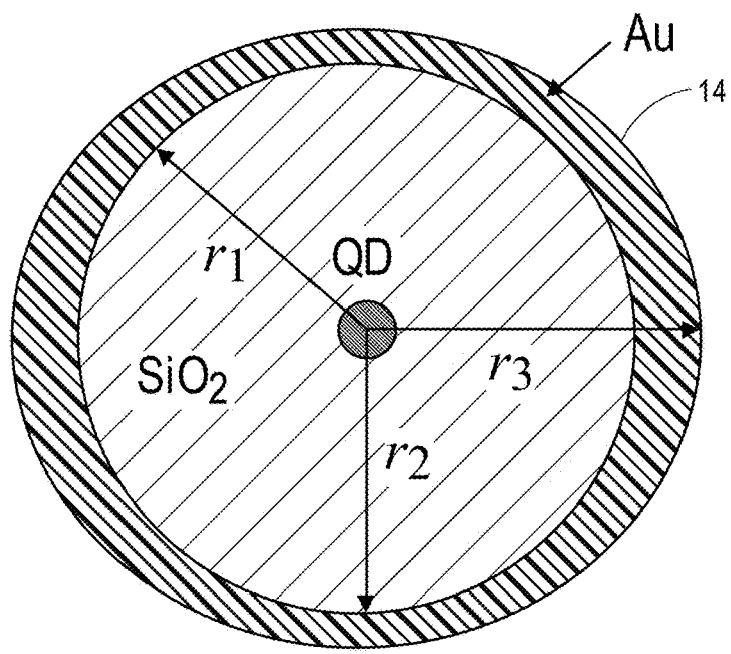
FIG. 4A illustrates a quantum dot encapsulated with a non-uniform metallic layer according to an embodiment of the present disclosure.

The metallic nanoshell can be a highly conformal, continuous layer so as to uniformly encapsulate all or a portion of the particle. Alternatively, the metallic nanoshell can be non-conformal and/or discontinuous. For example, the metallic nanoshell can comprises a dense array of metallic dots 30, as illustrated in FIG. 3. The metallic dots 30 can have a diameter of, for example, less than 3 nm. In another embodiment, the metallic nanoshell comprises a non-uniform metallic layer 14, as illustrated by FIG. 4A. The non-uniform metallic layer 14 can having a thickness that varies within, for example, the range of 0.2 nm to 6 nm. The thickness and uniformity of the metallic nanoshell can be optimized to provide an increased electric field enhancement, as desired.

Referring to FIG. 2, the radius, r1, of the dielectric coated Qd can range, for example, from about 5 nm to about 100 nm, such as about 10 nm to about 50 nm, such as about 15 nm to about 25 nm. In an embodiment, the radius, r2, of the plasmonic nanoparticle can range, for example, from about 6 nm to about 130 nm, such as about 15 nm to about 60 nm, such as about 20 nm to about 40 nm.

Figure 5:
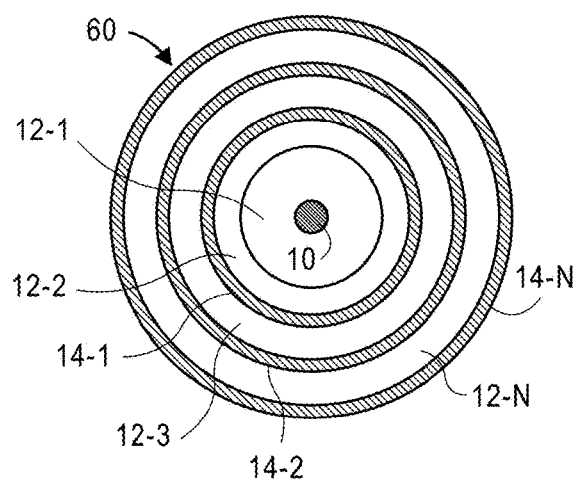
FIG. 5 illustrates a multi-shelled plasmonic nanoparticle (MSPN), according to an embodiment of the present disclosure.

FIG. 5 shows an example embodiment of a multi-shelled plasmonic nanoparticle (MSPN). The MSPN includes a semiconductor quantum dot 10, an optional dielectric layer 12-1 that is formed by liquid phase deposition and a dielectric layer 12-2 that is formed by ALD, by methods as described herein. Optional dielectric layer 12-1 and ALD dielectric layer 12-2 fully or partially encapsulate the quantum dot 10. A metal nanoshell 14-1 fully or partially encapsulates dielectric layers 12-1,12-2 and quantum dot 10. A further dielectric layer 12-3 fully or partially encapsulates conductive nanoshell 14-1. A further conductive nanoshell 14-2 fully or partially encapsulates dielectric layer 12-3. Still further dielectric layers 12-N and metal nanoshell layers 14-N can be employed, as shown in FIG. 5, where "N" represents the number of dielectric layers or metal nanoshell layers. Such structures are described in further detail in U.S. Pat. No. 9,267,889, the disclosure of which is incorporated herein by reference in its entirety, Each of the concentric dielectric layers 12-2 to 12-N and metal nanoshell layers 14-1 to 14-N can comprise any of the dielectric or metal layers described herein and can be formed by ALD techniques, as also described herein. The number of nanoshells, "N" can be any number. As an example; N for the metal nanoshell layers can range from 1 to 10, such as 2 to 4, while the associated number of dielectric layers would be whatever number will provide the desired dielectric separation between each of the metal nanoshells.

In appropriately-designed PQD structures, as elaborated further herein, the proposed dielectric and multi-layered metallic nanoshell layers will not only help enhance the electric fields in the center of the nanostructure, thus increasing the brightness of the nanoparticles, but will also chemically isolate the QDs from human tissue and significantly reduce the toxicity of such TPAF nanoparticles if used in biological applications.

In an embodiment, the plasmonic nanoparticles of the present disclosure can exhibit significant fluorescence intensity changes due to relatively sharp resonance peaks. Further, the absorption and emission properties can optionally be chosen to be optimal for wavelengths and intensities that are readily achievable from, for example, relatively standard commercial Ti-sapphire laser systems. It has been found that at a "nominal" intensity of, for example, 8 GW/cm$^2$, the TPAF signals from "bare" ultrasmall CdSe QDs at excitation wavelengths near 780 nm were observed to be ~8 times larger than those at 850 nm and ~68 times larger than those at 900 nm (See Wang, L. et al., "Maximization of nonlinear fluorescence from ultrasmall (≤2 nm) semiconductor quantum dots to be used for deep tissue imaging," Journal of the Optical Society of America B 26, 2161 (2009)), indicating that such a choice of QDs should be highly relevant for use in the optimization of the proposed PQDs.

In an embodiment, the particles of the present disclosure can be tuned to maximize the output signals for their effective use in biological imaging and luminescent marker applications. This can be done by: (a) using semiconductor materials with relatively high intrinsic quantum efficiencies, (b) optimizing the size of such quantum dots to obtain emission wavelengths that coincide with the availability of efficient photomultiplier or photodetector systems, (c) enhancing the TPAF signals via use of the best designs for plasmonic electric field enhancement (EFE) in the PQD structures, and (d) optimizing the choice of the excitation wavelengths for QDs chosen in accordance with the first two factors.

Figure 6:
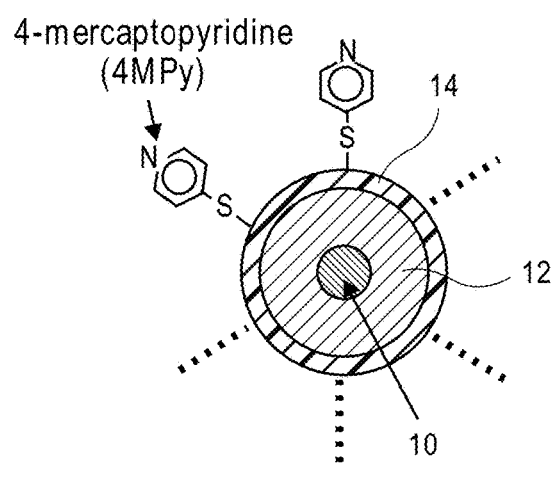
FIG. 6 illustrates a schematic diagram of a pH sensor with pH-sensitive ligands that may be functionalized on the outer surface of the proposed PQD nanoparticles to facilitate pH sensing via SERS measurements, according to an embodiment of the present disclosure.

In an embodiment, the plasmonic nanoparticles of the present disclosure can be configured for two-photon absorption-induced fluorescence (TPAF) imaging. This can be accomplished by the addition of one or more Surface Enhanced Raman Specroscopy (SERS) active molecules adsorbed on an outer surface of the metallic nanoshell. As shown in FIG. 6, the SERS active molecules may include, for example, 4-mercaptopyridine (4MPy) or 4-mercaptobenzoic acid (pMBA). Techniques for attaching such SERS molecules to the outer surface of the plasmonic nanoparticles are well known in the art.

In particular, the illustration of FIG. 6 shows a schematic diagram of a pH nanosensor. This nanosensor comprises a semiconductor quantum dot core 10, surrounded by an dielectric layer 12, which in turn is surrounded by an ultra-thin metal nanoshell 14. Any of the dielectric and/or metal layers described herein can be employed. In one example, the metal nanoshell is a gold or silver nanoshell. The outer layer of the nanoshell 14 is surrounded by an adsorbate of a SERS active molecule (also referred to herein as a ligand), such as pMBA or 4MPy. A feature of the nanoparticle of FIG. 6 is that it enables the simultaneous obtainment of a SERS "signature" signal along with an ultra-bright luminescence from the semiconductor quantum dot to facilitate ultra-precise spatial location of the source of the SERS emission. More specifically, the pH-sensitive SERS shifts in the chosen ligands, such as 4MPy, to provide pH information via the enhanced SERS in the plasmonic particle, while the TPA-induced fluorescence from the PQD core provides clear information on the location of the nanoparticle with micron or sub-micron spatial precision.

As stated above, a modality with which we will use this nanoparticle is by using 2-photon absorption enabled luminescence that occurs simultaneously in the PQD while using the same near-infrared excitation for near-infrared SERS spectroscopy on the surface of the PQD to measure analyte concentrations. One advantage of the PQD nanoparticle over conventional fluorescent quantum dots is the fact that enclosing the quantum dot inside the metallic nanoshell both provides a high enhancement of the local field within the shell, enabling high luminescence efficiency, as well as complete isolation of the quantum dot from the external environment, alleviating problems related to quantum dot toxicity and fluorescence blinking. The outer surface plasmonic enhancement in the proposed PQD will also cause significant enhancements of the SERS signals while enabling spatial information of the location of the measured analyte via the ultrabright TPAF luminescence.

In general, organic acids and bases serve effectively as pH sensitive ligands. The organic acids and bases are chosen based on their relative dissociation constants (Kds), stabilities, and measurable change in SERS signature on protonation/deprotonation. As implied in FIG. 6, pyridine, benzoic acid, and phenol-based compounds can be used as the base structures of the pH-ligands because their conjugated symmetric ring systems are highly Raman active and changes in the protonation state will dramatically affect the SERS spectrum. In particular, 4MPy is an excellent example of a pH-sensitive SERS reporter. This compound has been used frequently as a ligand since it is commercially available and well studied. Any other suitable pH sensitive ligand can be used in addition to or in place of 4MPy. It is noted that such molecules can be functionalized with substituents of varying bulk and electronic properties. These substituents will, in turn, shift the Kd and thus tune the pH sensitive region of the reporter. It is known that the molecules adsorbed on the surface of SERS particles are sensitive to locally changing chemical environments, and manifest themselves as changes in the SERS spectra. See, for example, Hu, J. et al., "Surface-enhanced Raman spectroscopy study on the structure changes of 4-mercaptopyridine adsorbed on silver substrates and silver colloids," Spectrochimica Acta Part A: Molecular and Biomolecular Spectroscopy, 58, 2827-2834, doi:10.1016/S1386-1425(02)00074-4, 2002, the disclosure of which is incorporated herein by reference in its entirety.

The sensors of the present disclosure can be employed in a variety of applications. For example, as mentioned above, the sensors can be used in methods for bio-sensing applications, pH sensing or Calcium ion sensing. The plasmonic particles can also be employed in methods for treating cancer. One such method comprises employing the plasmonic nanoparticle for enhancing light intensity for generation of reactive oxygen species (ROS) in light-induced destruction of malignant cancer cells. Such a method can comprise introducing a plurality of the plasmonic nanoparticles of the present disclosure into a patient to be treated for cancer and exciting the plasmonic particles with an illumination source so as to generate reactive ion species in the presence of cancer cells in the patient.

Figure 7:
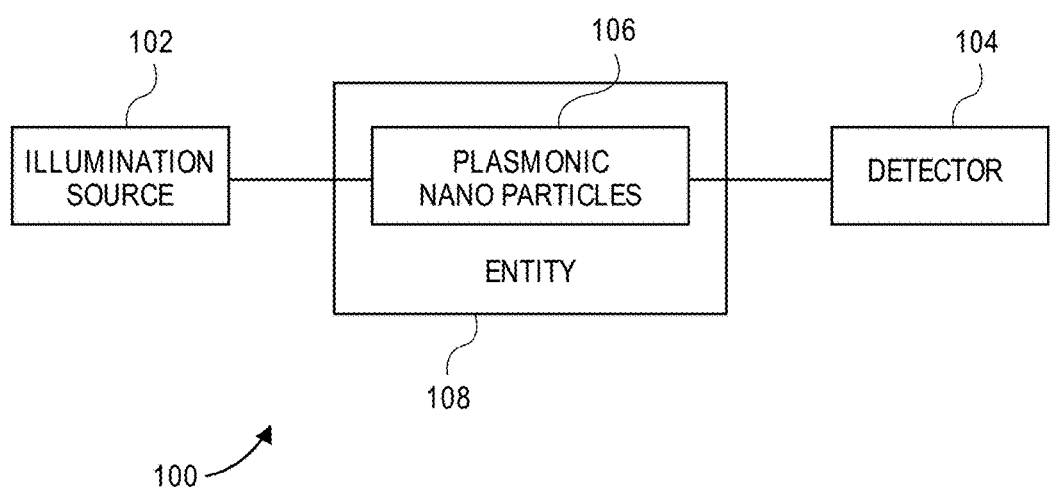
FIG. 7 is a block diagram of a nanosensor system, according to an embodiment of the present disclosure.

The plasmonic nanoparticles of the present disclosure can be employed as nanosensors for use in nanosensor systems. Referring to FIG. 7, an embodiment of such as nanosensor system 100 comprises an illumination source 102, an optical signal detector 104 and a plasmonic nanoparticle 106. The plasmonic nanoparticle 106 used as the nanosensor can be any of the plasmonic particles described herein. The plasmonic nanoparticle 106 can be contained in any desirable entity, such as a biological entity (e.g., a human or animal). Illumination source 102 can include, among other sources, a light source such as a laser. As would be understood by one of ordinary skill in the art, illumination source 102 can be implemented using a light source with associated optical elements to focus, steer, or wavelength shift output from the light source. The illumination source 102 can be selected based on the characteristics of the plasmonic nanoparticle 106. Alternatively, the plasmonic nanoparticle can be selected based on the characteristics of the illumination source. The selection of illumination source 102 and the plasmonic nanoparticle can be made considering characteristics of both the illumination source and the plasmonic nanoparticle in view of the application for which they are to be applied.

Detection device 104 can include imaging components and/or any other components suitable for detecting light generated by the plasmonic nanoparticles. Such components can include filters to separate light generated by the plasmonic nanoparticle in response to excitation light from an appropriate illumination source 102 from any light from the illumination source 102 that is reflected from entity 108 and the plasmonic nanoparticle. In addition, filters can be used to separate a number of signals that are generated by the plasmonic nanoparticle or the plasmonic nanoparticle in combination with other elements for measuring characteristics of entity 108. Detection device 104 can include data collection equipment such as imaging camera or various types of spectrographic equipment.

EXAMPLES

Example 1

The following examples are based on calculations performed using the Mie scattering theory with a vector spherical harmonic (VSH) model, as reported in Ru, E. L. et al., "Principles of Surface-Enhanced Raman Spectroscopy: and related plasmonic effects," (Elsevier Science: 2008). The calculations were made based on bulk dielectric constants for Ag and Au at several wavelengths corresponding to optimal TPAF excitation of a PQD containing a 6 nm CdSe QD as a function of the noble metal film thicknesses and the dielectric permittivity of the spacer dielectrics (with silica and titania—with relative permittivities of 2.3 and 6.2—as the most promising candidates as practical dielectrics).

Figure 8:
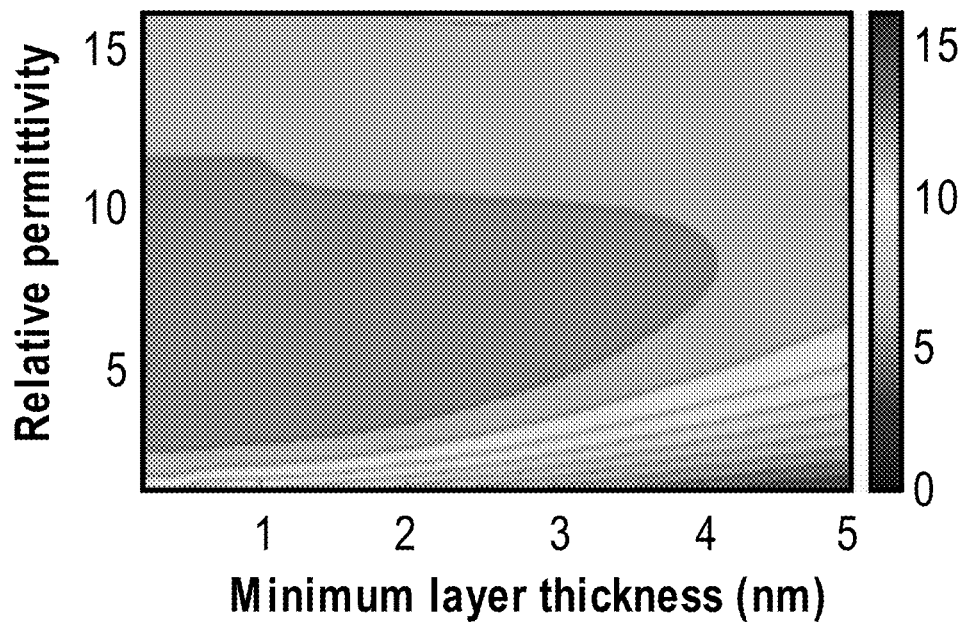
FIG. 8 illustrates a 2-dimensional "false color" plot of the magnitude of the computed EFE at the center of the PQD as a function of the Ag layer thickness and the relative permittivity of the dielectric spacer for an incoming plane wave at a wavelength of 800 nm, according to an example of the present disclosure.
Figure 9:
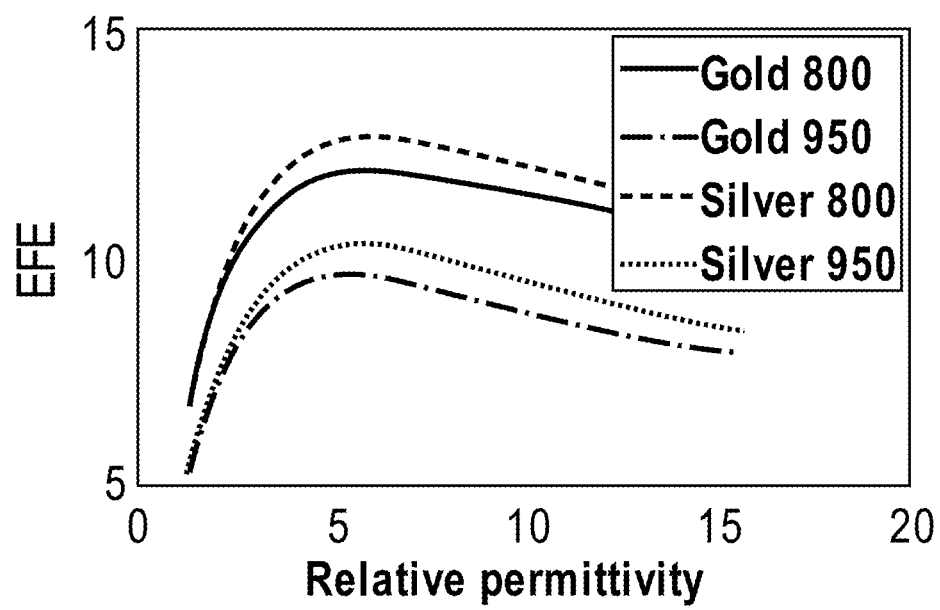
FIG. 9 is a plot depicting the EFE as a function of relative dielectric permittivity for Au and Ag films of 2.6 nm, according to an example of the present disclosure.

FIG. 8 shows a representative plot of such computations, more specifically depicting a 2-dimensional "false color" plot of the magnitude of the computed EFE at the center of the PQD as a function of the Ag layer thickness and the relative permittivity of the dielectric spacer for an incoming plane wave at a wavelength of 800 nm. Similar computations were performed for Au films over a broad range of wavelengths. FIG. 9 summarizes some of these results by depicting the EFE as a function of relative dielectric permittivity for Au and Ag films of 2.6 nm, indicating very clearly that EFEs of over 12 (and enhancements of TPAF signals by 20,000) may potentially be obtained using relatively simple Au/Ag-titania-encapsulated quantum dots of practical dimensions.

Example 2

Figure 10A:
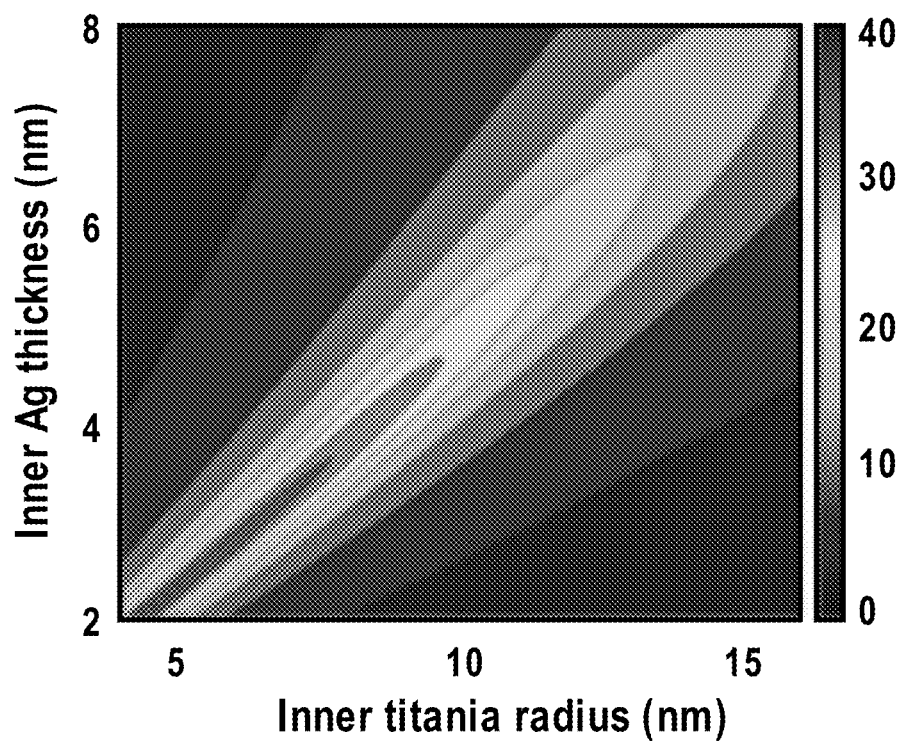
FIG. 10A is a plot depicting EFE for a 2-metal-shell plasmonic particle as a function of innermost layer thicknesses, according to an example of the present disclosure.
Figure 10B:
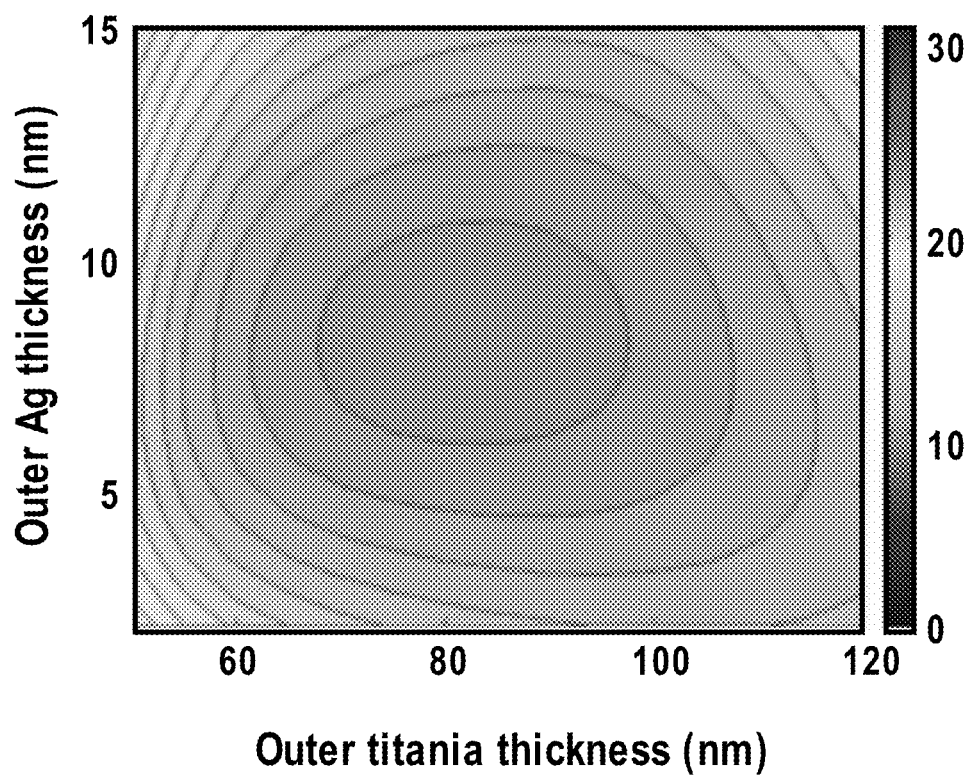
FIG. 10B is a plot depicting EFE for a 2-shell plasmonic particle as a function of outermost layer thicknesses, according to an example of the present disclosure.
Figure 10C:
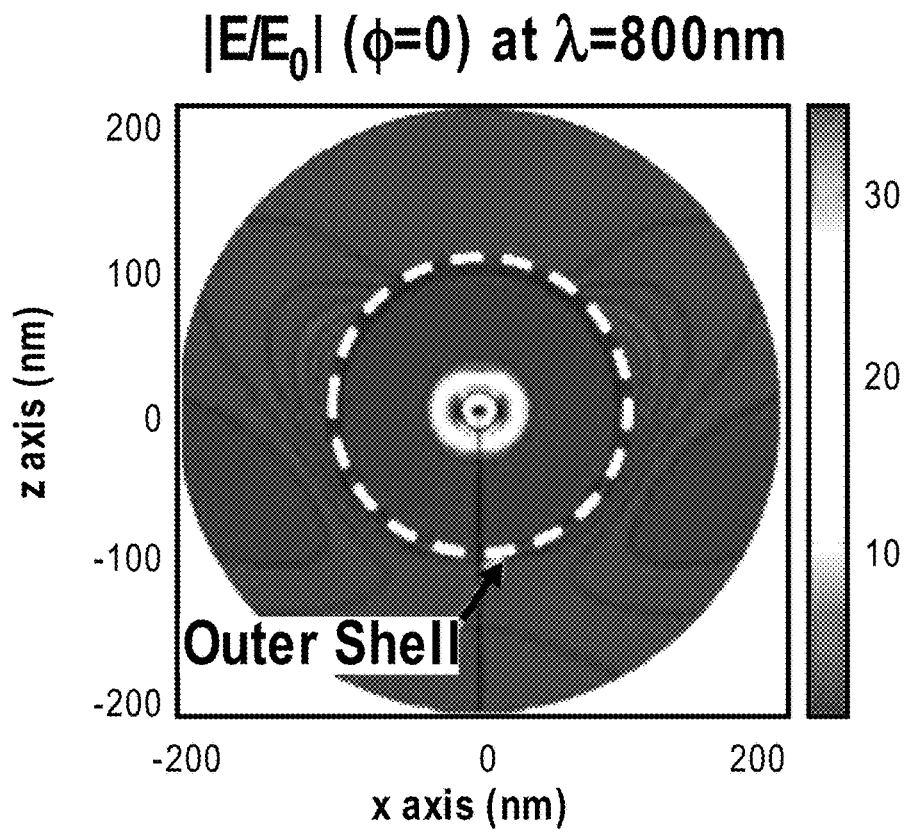
FIG. 10C is a plot showing spatial distribution of EFE for a 2-shell plasmonic particle, according to an example of the present disclosure.
Figure 10D:
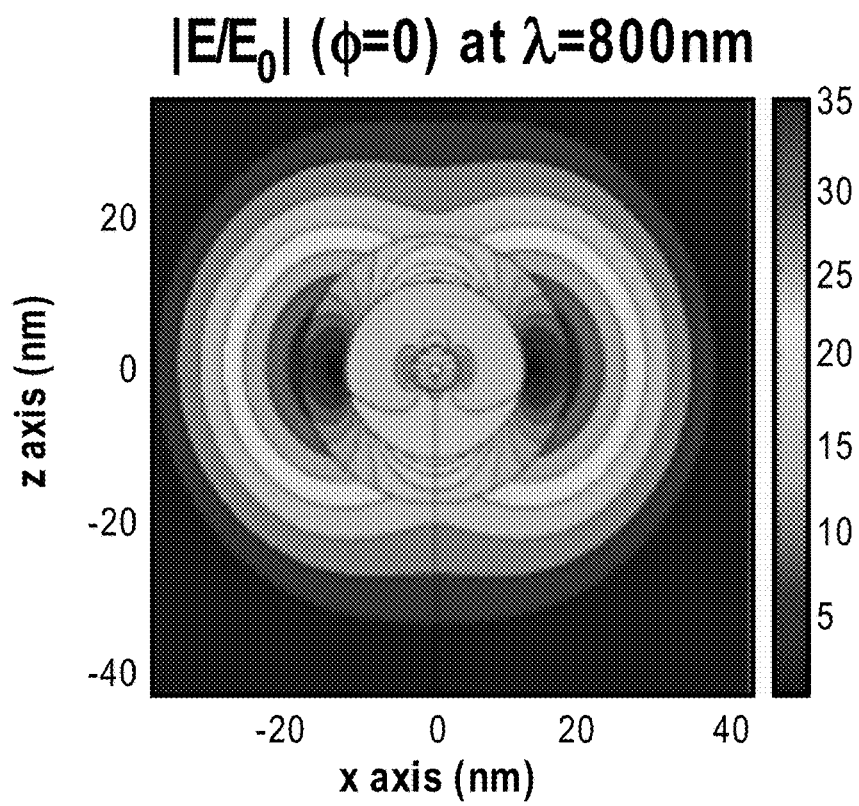
FIG. 10D is a plot showing magnified spatial EFE plot for 2-shell plasmonic particle, according to an example of the present disclosure.

Because nanoshells of thicknesses <3 nm may be difficult to fabricate reliably, alternate multilayered and multishelled nanostructures were explored with larger metal film thicknesses and relatively high EFEs. As shown in the preliminary calculations of FIG. 10, which depicts the case of a multilayered nanostructure with 2 silver shells and titania dielectric spacers, much larger enhancements in the EFE may be achieved at the luminescence source (the QD core) and at the outer SERS (surface-enhanced Raman scattering) active surface even with just a first level of optimization of the device dimensions. For this example, based on an excitation wavelength of 800 nm, with an 8 nm thick Ag outer shell and an 80 nm outer diameter titania (relative permittivity of 6.2), the maximum EFE increases with small layer thicknesses; however, even for an inner gold layer as large as 6 nm the maximum EFE observed was over 23, corresponding to an anticipated maximum TPAF signal enhancement of over 280,000, and an anticipated TPAF signal enhancement of over 200,000 over a broad range of relatively practical nanoparticle dimensions. A spatial field enhancement plot of this optimal structure is shown in FIG. 10C and a "zoomed-in" plot for the inner layers shown in FIG. 10D. The anticipated EFEs on the surface of the outer shell were larger than 35, corresponding to anticipated SERS signal enhancements of over 1.5 million. This "first-level optimized" structure corresponds to a 12 nm radius inner titania layer, 6 nm thick inner Ag shell, 80 nm thick outer titania layer, and an outer Ag shell of 8 nm thickness. Even though this structure is larger and a little more complex, it should be much easier to fabricate because of the larger metal film thicknesses needed, and should be very usable for several of the intended applications, such as TPAF-based nonlinear in vivo imaging of vascular tissue. See Larson, Daniel R., et al., "Water-Soluble Quantum Dots for Multiphoton Fluorescence Imaging in Vivo," Science 300 (5624) (May 30): 1434-1436.

Example 3

Figure 4B:
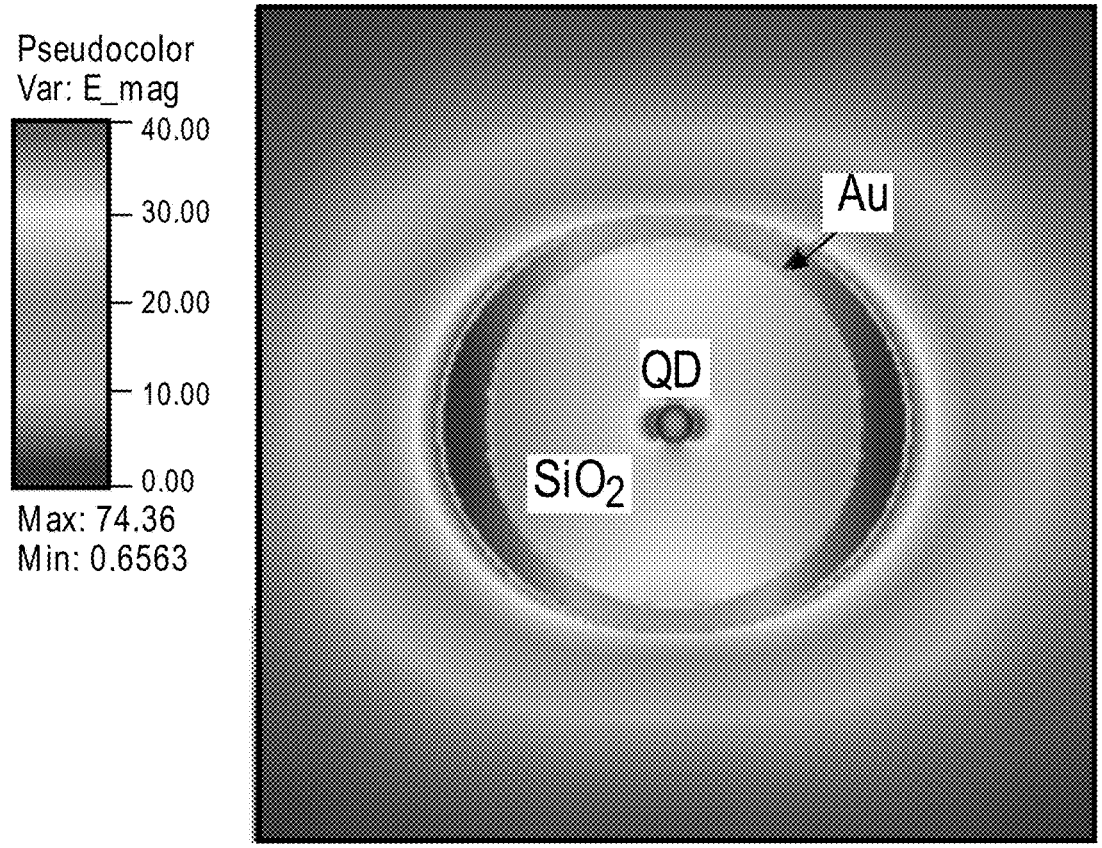
FIG. 4B depicts the spatial distribution of the EFE for a plasmonic nanoparticle, similar to that shown in FIG. 4A, with a mean silica radius of 23 nm and an excitation wavelength of 800 nm, according to an example of the present disclosure.

Another representative example of a composite nanoparticle, as illustrated in FIG. 4A, is for the case of a QD core/silica shell/gold shell (QDSG) in which the outer gold shell is nonuniform, (the model employed a metal layer thickness that varied from 3 nm to 6 nm). The radius, $r_1$, was 23 nm; $r_2$ was 26 nm and $r_3$ was 29 nm. The physical importance of modeling such a structure lies in the fact that for small metal film thicknesses, thin film deposition techniques often likely lead to non-uniform (and sometimes discontinuous) metal shells. In order to obtain high-accuracy and rapid simulations of such nonuniform shells, a novel multi-trace boundary integral equation (BIE) method was employed. Compared to existing numerical methods, such as differential equation based methods, the BIE method provides several significant advantages, including: (a) very high accuracy for high density composite materials, and a need for much fewer unknowns for precise solutions, (b) much more robust preconditioning and rapid convergence for composites involving multi-scale geometry features, (c) rapid and accurate virtual prototyping of the PQD structures. FIG. 4B depicts the spatial distribution of the EFE for a QDSG nanoparticle with a mean silica radius of 23 nm and an excitation wavelength of 800 nm. It was observed that the EFEs on the surface of the outer shell were larger than 40, the field enhancement outside the quantum dot in the QDSG structure reached a value of 35, and the field enhancement was approximately a factor of 8 near the center of the quantum dot, strongly indicating the promise of such nanostructures for TPAF applications. The use of titania leads to much higher field enhancements, as indicated in Table 1 below.

Example 4

Modelling as described in Example 1 was employed to estimate EFEs for plasmonic nanoparticles having various material combinations and the results are shown in Table 1. It is useful to point out that EFE's of over 5 were also obtained with several other metal-insulator combinations, including Pt, Pd, Ni, and Cu with appropriately chosen metal film and insulator thicknesses, permitting several choices of materials combinations for the proposed plasmonic quantum dots, although Au and titania are the preferred metal and insulator choices.

TABLE 1

EFE's estimated for the highly uniform PQD structures corresponding to the simple near-ideal PQDs of FIG. 4A

| Dielectric | Metal | High Uniformity Required | EFE @ $\lambda$ = 800 nm | EFE @ $\lambda$ = 950 nm |
|---|---|---|---|---|
| $SiO_2$ | Ag | yes | 8 | 5.5 |
| $SiO_2$ | Au | yes | 7 | 4.5 |
| $TiO_2$ | Ag | yes | 23 | 18 |

Example 5

Figure 11:
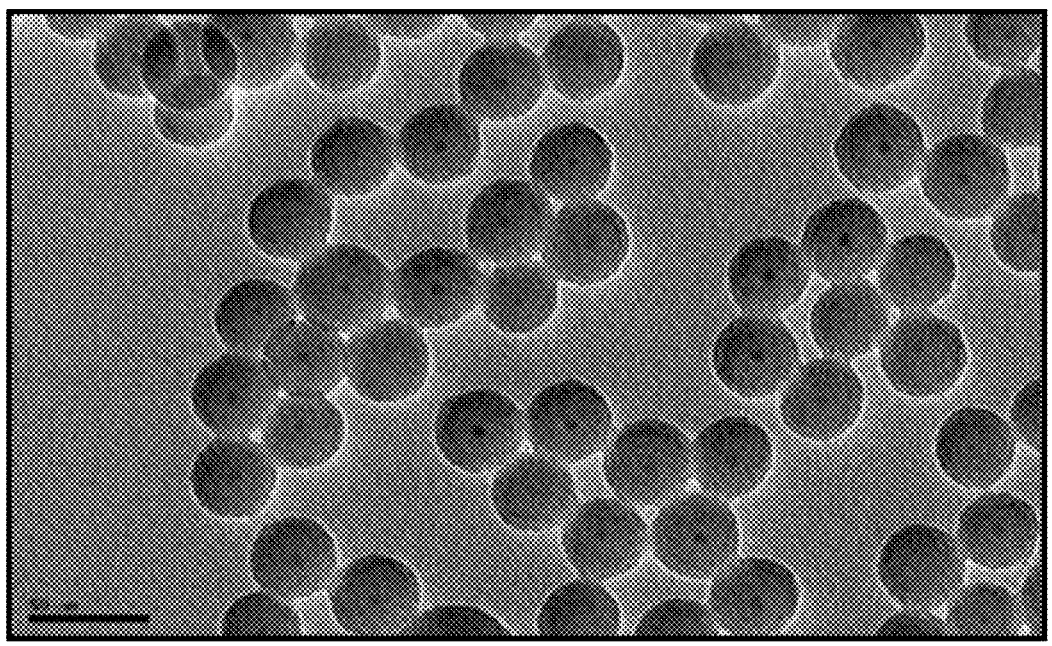
FIG. 11 shows 35 nm silica shells uniformly coating QDs prepared using a microemulsion route involving TEOS as a silica source. The 6 nm QDs can be seen as dark spots, and the scale corresponds to 50 nm.

CdSe/ZnS QDs having a size variation of better than 5% were obtained commercially from Ocean Nanotech. These quantum dots were coated with silica using a coating technique described generally in the literature. The approach including using a reverse microemulsion where the QD, tetraethylorthosilicate (TEOS) and ammonia were localized within reverse micelles resulting in the growth of a silica layer on the QD. A TEM image of the silica-coated QDs from the inventors preliminary work is shown in FIG. 11, in which silica spheres with a diameter <35 nm and a dark QD "core" are evident, as described in Klopfer, M. et al., Plasmonic quantum dots for nonlinear optical applications" Opt. Mater. Express 1, 1353-1366 (2011). The method of synthesis is flexible in that the thickness of the silica layer can be controlled and it allows us to generate uniform coatings of silica on the QDs without affecting their optical properties.

All of the published documents recited in this disclosure are incorporated herein by reference in their entireties. If there is a conflict between any definition of a term recited in any of the incorporated documents and a term recited in this disclosure, the meaning of the term as determined by the text of this disclosure absent the incorporations by reference is controlling.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein.

While the present teachings have been illustrated with respect to one or more implementations, alterations and/or modifications can be made to the illustrated examples without departing from the spirit and scope of the appended claims. In addition, while a particular feature of the present teachings may have been disclosed with respect to only one of several implementations, such feature may be combined with one or more other features of the other implementations as may be desired and advantageous for any given or particular function. Furthermore, to the extent that the terms "including," "includes," "having," "has," "with," or variants thereof are used in either the detailed description and the claims, such terms are intended to be inclusive in a manner similar to the term "comprising." Further, in the discussion and claims herein, the term "about" indicates that the value listed may be somewhat altered, as long as the alteration does not result in nonconformance of the process or structure to the illustrated embodiment. Finally, "exemplary" indicates the description is used as an example, rather than implying that it is an ideal.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompasses by the following claims.

What is claimed is:

1. A method of making free-standing ALD-coated plasmonic nanoparticles comprising:
   providing a plurality of semiconductor quantum dots;
   depositing one or more conformal layers of dielectric material over the quantum dots to form dielectric-coated quantum dots; and
   depositing a conformal metallic nanoshell over the dielectric-coated quantum dots to form plasmonic nanoparticles,
   wherein at least one layer chosen from i) the conformal layers of dielectric material and ii) the conformal metallic nanoshell is deposited using a vapor phase atomic layer deposition (ALD) process, and
   wherein the plasmonic nanoparticles are free-standing.

2. The method of claim 1, further comprising dispersing the semiconductor quantum dots on a support comprising sacrificial material prior to the depositing the one or more conformal layers of dielectric material; and removing the sacrificial support after the depositing the conformal metallic nanoshell to form the free-standing ALD-coated plasmonic nanoparticles.

3. The method of claim 2, wherein removing the sacrificial support comprises burning out or vaporizing the sacrificial material.

4. The method of claim 1, wherein the ALD process comprises:
   a) placing the semiconductor quantum dots on a sacrificial support under vacuum at a temperature in the range of 80° C. to 250° C.;
   b) forming a chemisorbed monolayer of a first reactant on at least a portion of a surface of the semiconductor quantum dots;
   c) forming an atomic layer of a material over the semiconductor quantum dots by reacting a second reactant with the chemisorbed monolayer of the first reactant;
   d) repeating steps b) and c) to achieve a desired layer thickness,
   wherein between each step a), b), c) and d), vacuum is applied to remove an excess of first reactant, second reactant, and reaction byproducts, and any weakly bonded physi-sorption layer on the surface of the quantum dot.

5. The method of claim 4 further comprising adding a third reactant and optionally a fourth reactant to form a coating with ternary or quaternary compositions, respectively.

6. The method of claim 4, wherein the dielectric material is alumina, $Al_2O_3$; the first reactant is trimethyl aluminum (TMAl) and the second reactant is water.

7. The method of claim 4, wherein the dielectric material is titania, $TiO_2$; the first reactant is titanium tetrachloride ($TCl_4$) and the second reactant is water.

8. The method of claim 4, wherein the conformal metallic nanoshell comprises palladium and is formed by the ALD process employing $Pd(hfac)_2$ as the first reactant and hydrogen as the second reactant.

9. The method of claim 1, further comprising, prior to the depositing the one or more conformal layers of dielectric material, coating the semiconductor quantum dots with silica using a liquid phase sol-gel method to form silica-coated quantum dots having a size suitable for vapor phase atomic layer deposition (ALD).

10. The method of claim 1, wherein the plurality of semiconductor quantum dots have diameters of less than 6 nm.

11. The method of claim 10, wherein the semiconductor quantum dot comprises at least one material selected from the compositions of CdSe/ZnS, CdSe/CdS and ZnSe/ZnS.

12. The method of claim 10, wherein the semiconductor quantum dot is a fluorophore, the plasmonic nanoparticle further comprising a second fluorophore selected from the group consisting of semiconductor nanoparticles or organic dyes such as fluorescein and rhodamine.

13. The method of claim 10, wherein the metallic nanoshell comprises one or more metals selected from gold, silver, platinum, palladium, aluminum, copper, and nickel.

14. The method of claim 1, wherein the metallic nanoshell comprises an array of metallic dots, the metallic dots having a diameter of less than 3 nm.

15. The method of claim 1, wherein the metallic nanoshell comprises a non-uniform metallic layer having a thickness in the range of 0.2 nm to 6 nm.

16. The method of claim 1, wherein the metallic nanoshell is a multilayered metallic nanoshell, wherein each layer has a unique composition.

17. The method of claim 1, wherein the one or more conformal layers of dielectric material comprise a material chosen from the compounds of silica, titania and alumina.

18. The method of claim 1, wherein the semiconductor quantum dot comprises at least one material selected from the compositions of CdSe/ZnS, CdSe/CdS and ZnSe/ZnS.

19. The method of claim 18, wherein the semiconductor quantum dot is a fluorophore, the plasmonic nanoparticle further comprising a second fluorophore selected from the group consisting of semiconductor nanoparticles or organic dyes such as fluorescein and rhodamine.

20. The method of claim 18, wherein the metallic nanoshell comprises one or more metals selected from gold, silver, platinum, palladium, aluminum, copper, and nickel.

21. The method of claim 18, wherein the metallic nanoshell comprises an array of metallic dots, the metallic dots having a diameter of less than 3 nm.

22. The method of claim 18, wherein the metallic nanoshell comprises a non-uniform metallic layer having a thickness in the range of 0.2 nm to 6 nm.

23. The method of claim 18, wherein the metallic nanoshell is a multilayered metallic nanoshell, wherein each layer has a unique composition.

24. The method of claim 23, wherein the one or more conformal layers of dielectric material comprise a material chosen from the compounds of silica, titania and alumina.

25. The method of claim 24, wherein the plurality of semiconductor quantum dots have diameters of less than 6 nm.

* * * * *